United States Patent
Melvin

(10) Patent No.: US 6,733,510 B1
(45) Date of Patent: May 11, 2004

(54) ARTICLE AND METHOD FOR COUPLING MUSCLE TO A PROSTHETIC DEVICE

(75) Inventor: David B. Melvin, Loveland, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/889,195

(22) PCT Filed: Jan. 12, 2000

(86) PCT No.: PCT/US00/00773

§ 371 (c)(1),
(2), (4) Date: Nov. 6, 2001

(87) PCT Pub. No.: WO00/41631

PCT Pub. Date: Jul. 20, 2000

Related U.S. Application Data

(60) Provisional application No. 60/115,727, filed on Jan. 12, 1999.

(51) Int. Cl.⁷ .............................................. A61B 17/04
(52) U.S. Cl. .................... 606/148; 606/228; 606/232
(58) Field of Search .................... 606/151, 222, 606/223, 224, 225, 213, 219, 232, 168; 623/13.19, 13.2, 14.13

(56) References Cited

U.S. PATENT DOCUMENTS

| | | |
|---|---|---|
| 3,176,316 A | 4/1965 | Bodell |
| 4,149,277 A | 4/1979 | Bokros |
| 4,187,558 A | 2/1980 | Dahlen et al. ........................ 3/1 |
| 4,255,820 A | 3/1981 | Rothermel et al. ................. 3/1 |
| 4,453,537 A | 6/1984 | Spitzer ........................... 128/1 |
| 4,519,392 A | 5/1985 | Lingua |
| 4,585,458 A | 4/1986 | Kurland ....................... 623/13 |
| 4,597,766 A | 7/1986 | Hilal et al. .................... 623/13 |
| 4,713,075 A | 12/1987 | Kurland ........................ 623/13 |
| 4,773,910 A | 9/1988 | Chen et al. ..................... 623/13 |
| 4,846,831 A | 7/1989 | Skillin ............................. 623/3 |
| 4,917,700 A | 4/1990 | Aikins .......................... 623/13 |
| 4,946,377 A | 8/1990 | Kovach ......................... 623/13 |
| 4,964,414 A | 10/1990 | Handa et al. ................. 128/784 |
| 5,049,155 A | 9/1991 | Bruchman et al. ............. 623/17 |
| 5,061,283 A | 10/1991 | Silvestrini ..................... 623/13 |
| 5,116,372 A | 5/1992 | Laboureau .................... 623/13 |
| 5,197,983 A | 3/1993 | Berman et al. ................ 623/13 |
| 5,217,495 A | 6/1993 | Kaplan et al. ................. 623/13 |
| 5,443,504 A | 8/1995 | Hill |
| 5,456,715 A | 10/1995 | Liotta |
| 5,643,308 A | 7/1997 | Markman |
| 5,667,526 A | 9/1997 | Levin |
| 5,697,978 A | 12/1997 | Sgro ............................ 623/12 |
| 5,957,977 A | 9/1999 | Melvin ........................... 623/3 |
| 5,981,827 A | 11/1999 | Devlin et al. ................. 623/16 |
| 6,214,047 B1 | 4/2001 | Melvin ..................... 623/11.11 |
| 6,221,103 B1 | 4/2001 | Melvin ........................ 623/3.1 |

OTHER PUBLICATIONS

Geddes et al (1991), Power Capability of Skeletal Muscle to Pump Blood, *Trans Am Soc. Artif. Intern Organs*, vol. XXXVII, pp. 19–23.

(List continued on next page.)

Primary Examiner—Michael J. Milano
Assistant Examiner—P Roberts
(74) Attorney, Agent, or Firm—Wood, Herron & Evans, LLP

(57) ABSTRACT

An insertion kit for positioning a plurality of filaments into muscle includes at least one holder that is configured for being attached to an end portion of the muscle. The holder is coupled with a guide, such as on a frame. The guide conforms the muscle to a desired shape. An inserter, used in conjunction with a plurality of needles, inserts a plurality of filaments into the muscle.

35 Claims, 22 Drawing Sheets

OTHER PUBLICATIONS

Salmons et al (1992), Cardiac Assistance From Skeletal Muscle: a Critical Appraisal of the Various Approaches, *British Heart Journal*, vol. 68, pp. 333–338.

Reichenbach et al (1994), Characterization and Work Optimization of Skeletal Muscle as a VAD Power Source, *ASAIO Journal*, pp. M359–M363.

Farrar et al (1992), A New Skeletal Linear–pull Energy Convertor as a Power Source for Prosthetic Circulatory Support Devices, *Journal of Heart and Lung Transplantation*, pp. S341–S349.

Reichenbach et al (1997), In Vivo Studies of an Implantable Energy Convertor for Skeletal Muscle Powered Cardiac Assist, *ASAIO Journal*, Vol 43, pp. M668–M672 (and Abstract).

Farrar et al (1995), Mechanical Advantage of Skeletal Muscle as a Cardiac Assist Power Source, *ASAIO Journal*, pp. M481–M484.

Sasaki et al (1992), A Skeletal Muscle Actuator for an Artifical Heart, *ASAIO Journal*, pp. M507–M511.

Acker et al (1987), Skeletal Muscle as the Potential Power Source for a Cardiovascular Pump: Assessment in Vivo, *Science*, vol. 236, pp. 324–327.

Melvin et al (1997), Coupling of Skeletal Muscle to a Prosthesis for Circulatory Support, *ASAIO Journal*, vol. 43, pp. M434–M441.

Ugolini (1986), Skeletal Muscle for Artificial Heart Drive: Theory and in Vivo Experiments, *Biomechanical Cardiac Assist*, pp. 193–211.

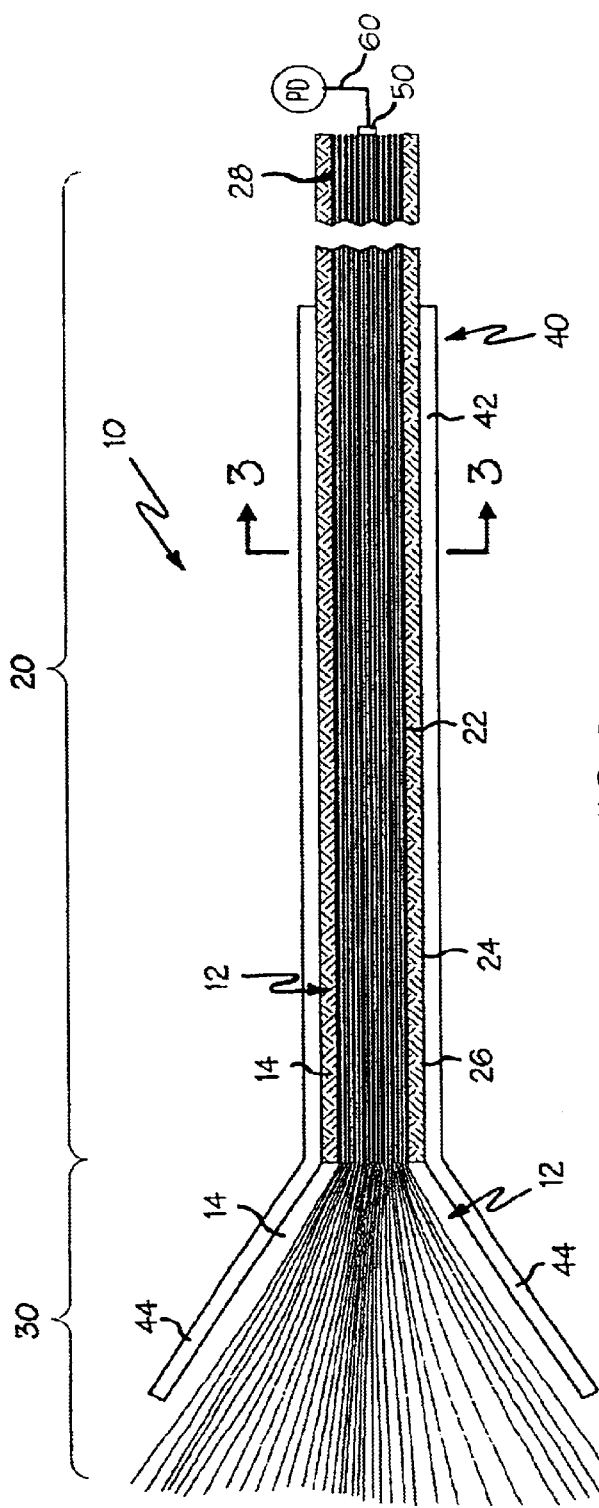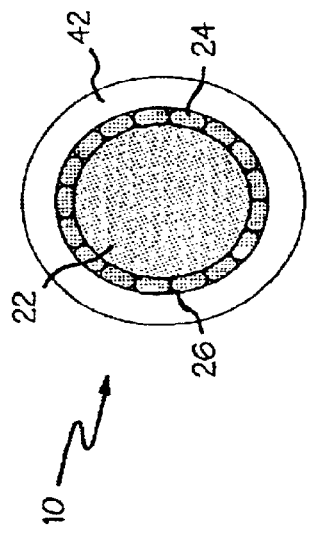

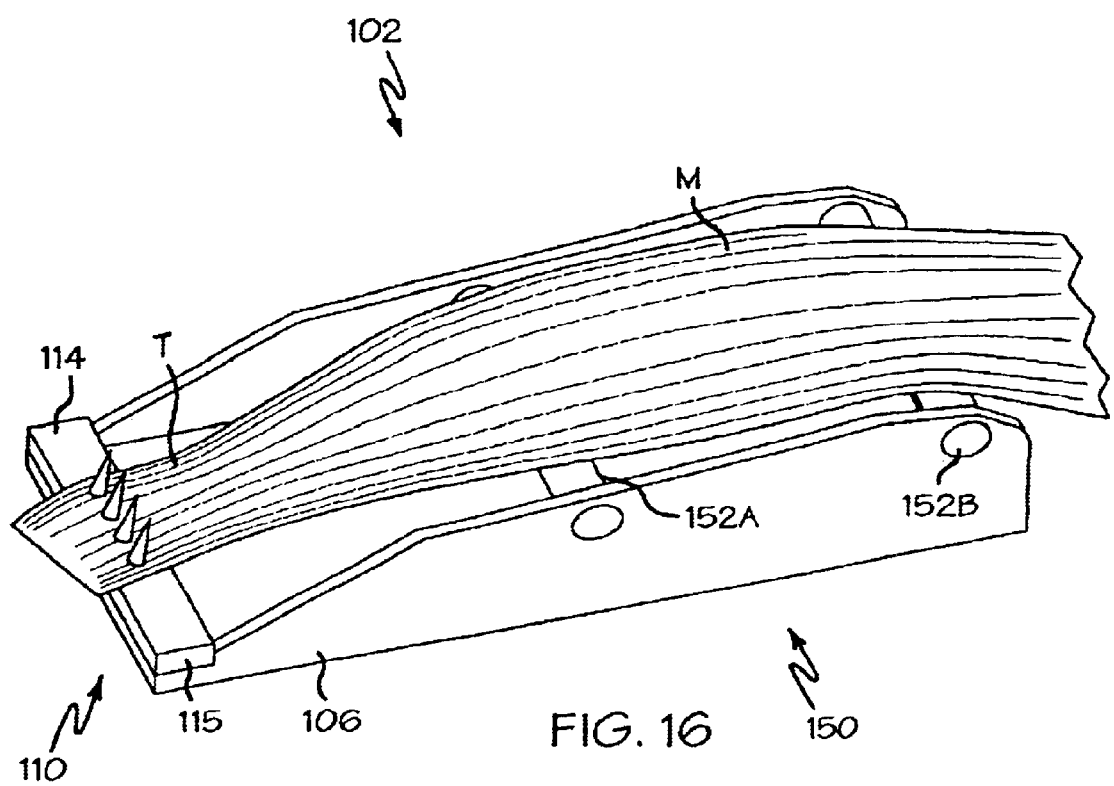

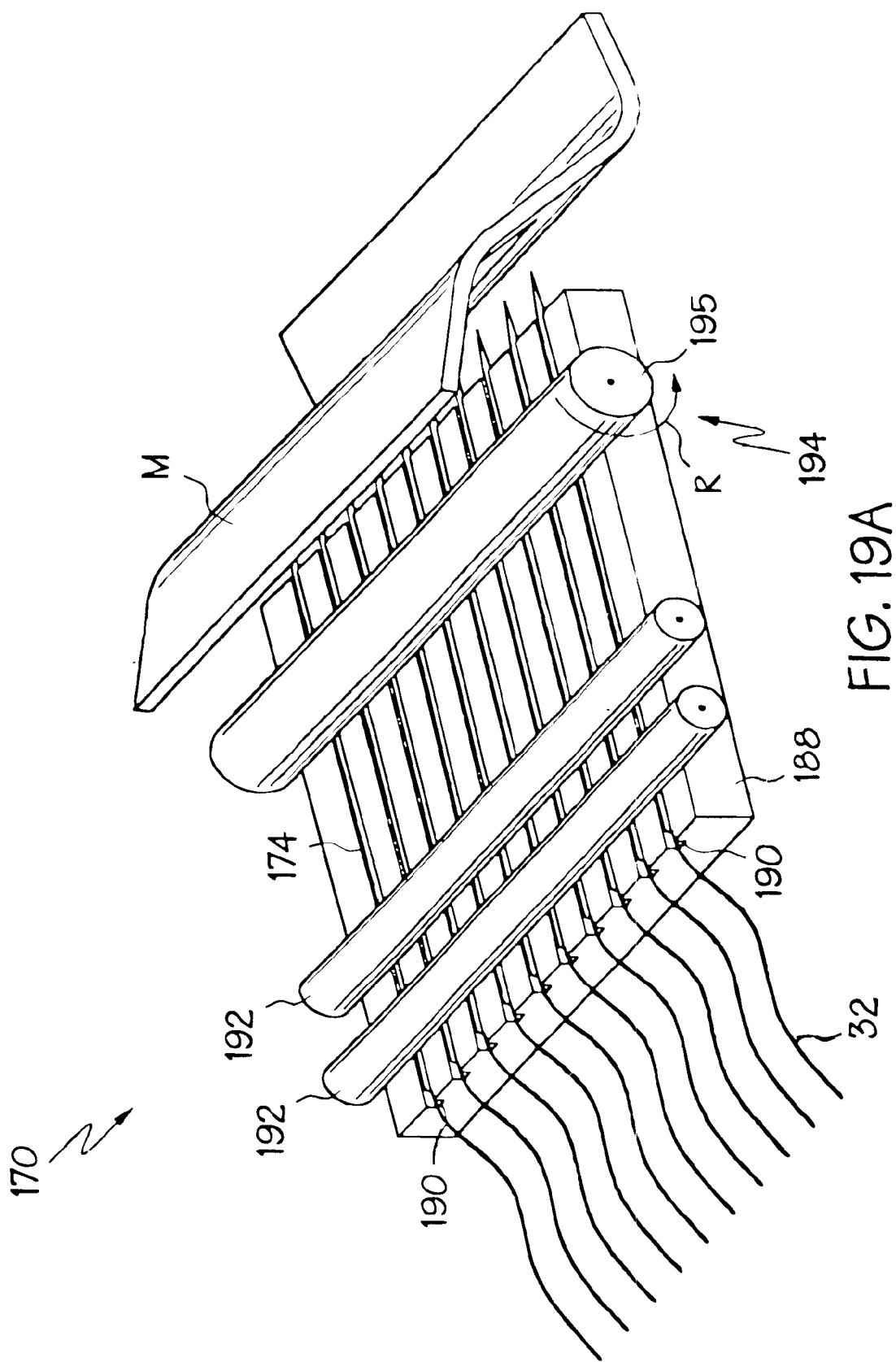

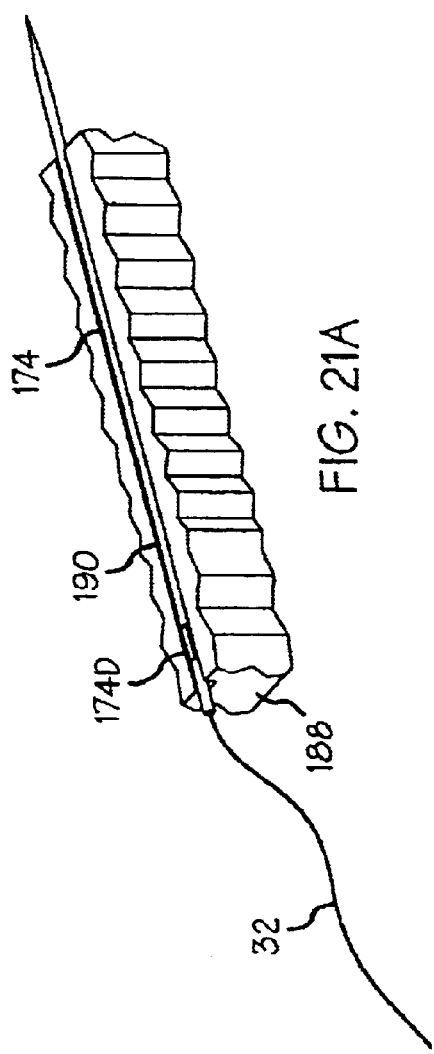
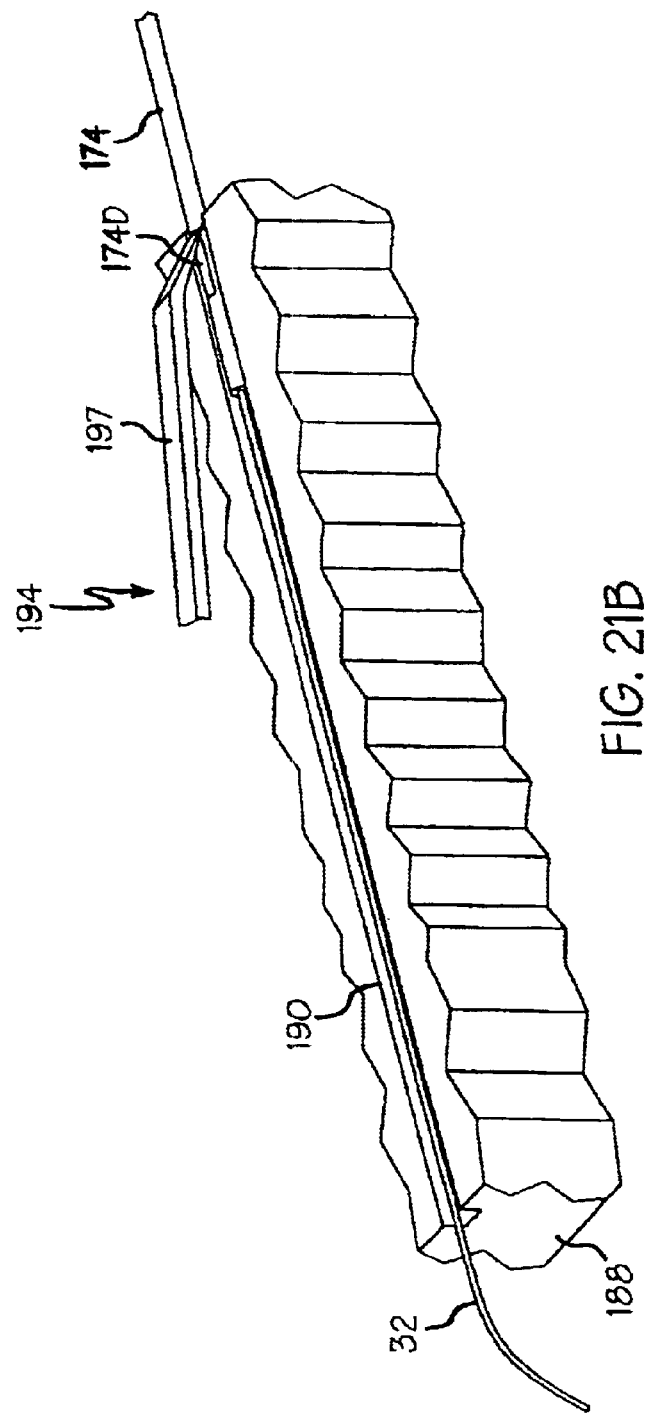

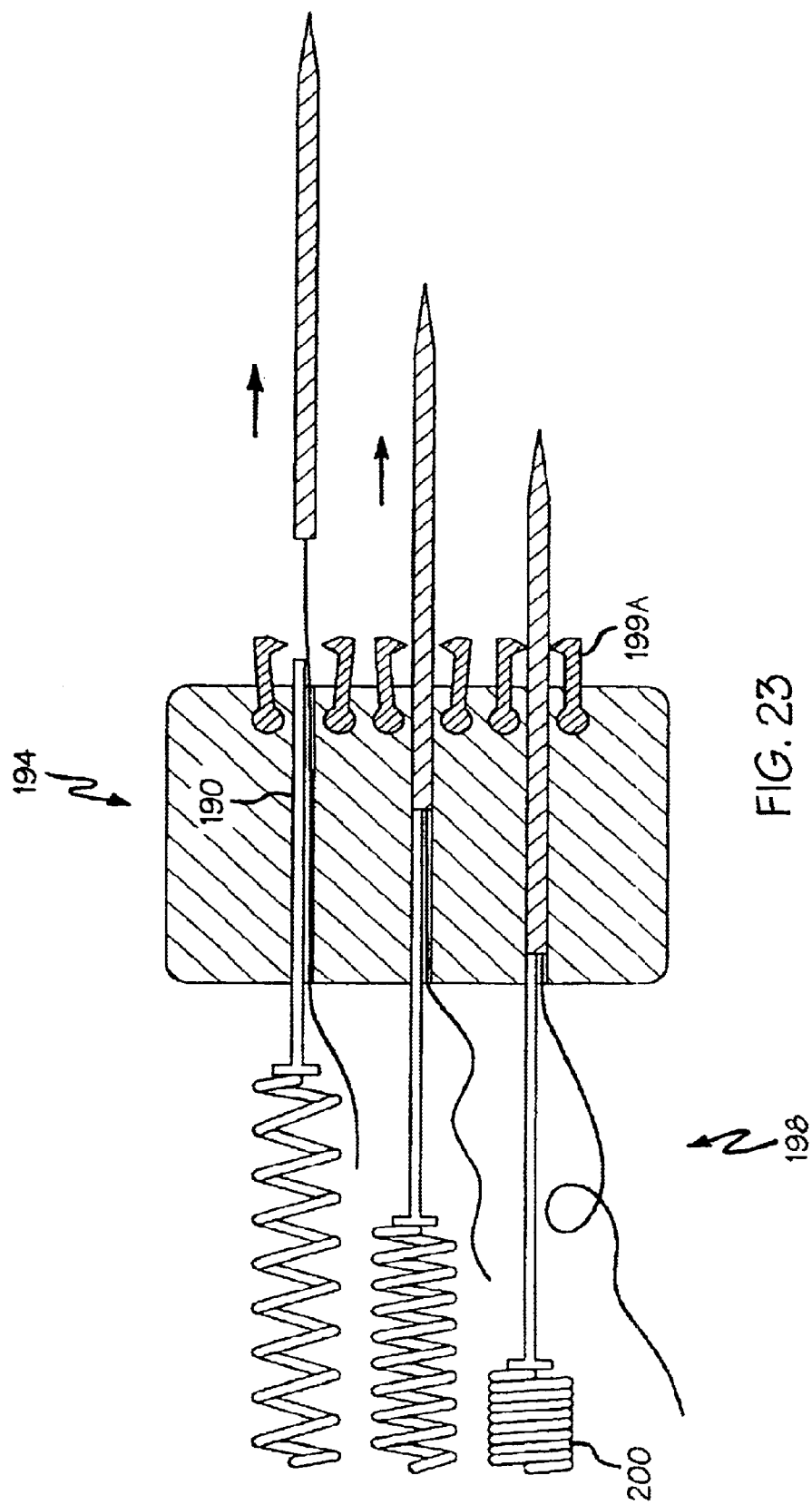

ARTICLE AND METHOD FOR COUPLING MUSCLE TO A PROSTHETIC DEVICE

The present application claims priority from co-pending U.S. Provisional Patent Application Serial No. 60/115,727, filed Jan. 12, 1999; and co-pending U.S. patent application Ser. No. 09/037,821, filed Mar. 10, 1998, to which this application is a Continuation-In-Part, the disclosures of which are hereby incorporated herein by reference.

TECHNICAL FIELD OF THE INVENTION

The present invention relates to a device and method for coupling skeletal muscle to a prosthetic device or bone and more specifically, a device and method for providing a mechanical linkage to actuate a prosthetic device or bone in response to skeletal muscle's linear contraction.

BACKGROUND OF THE INVENTION

An increasing number of people die annually from heart failure. The natural heart. and specifically, the cardiac muscle tissue of the natural heart (e.g., myocardium) can fail for various reasons to a point where the natural heart cannot provide sufficient circulation of blood for a body so that life can be maintained or can completely fail. Heart failure can be due to a variety of causes and/or reasons, including viral disease, idiopathic disease, valvular disease (mitral, aortic and/or both), ischemic disease, Chagas' disease and so forth. As a solution for the dysfunctional, failing and/or diseased natural heart, attempts have been made in the past to provide a treatment and/or device to assist in or entirely maintain blood circulation.

One approach to treat a failing heart has been to transplant a heart from another human or animal into a patient. The transplant procedure requires removing an existing organ (i.e., the natural heart) for substitution with another organ (i.e., another natural heart) from another human, or potentially, from an animal. Before replacing an existing organ with another, the substitute organ must be "matched" to the recipient, which can be, at best, difficult and time consuming to accomplish. Furthermore, even if the transplanted organ matches the recipient, a risk still exists that the recipient's body will reject the transplanted organ and attack it as a foreign object. The number of potential donor hearts is far less than the number of patients in need of a transplant. Although use of animal hearts would lessen the problem with fewer donors than recipients, there is an enhanced concern with the recipient body's rejection of the animal heart.

Another treatment and therapy for congestive heart failure has been to wrap skeletal muscle around the epicardial surface of the patient's own heart. Skeletal muscle can be an alternative to electromechanical systems (e.g., artificial hearts and/or ventricular assist devices), and thus may eliminate the need for an external power sources, skin penetrating power sources, or electrical induction. In a cardiomyoplasty procedure, skeletal muscle can be surgically removed from its natural anatomical position, such as across the back in the case of the latisimus dorsi muscle. Then, it is wrapped around the heart, allowed to heal, and reconditioned from a fast twitch muscle, which is susceptible to fatigue to a muscle with slow-twitch muscle fibers capable of chronic periodic contractions and that is generally fatigue resistant.

Use of a skeletal muscle wrap to power an existing natural heart has several drawbacks. Vascular interruption to the skeletal muscle while it is being removed and transplanted around the heart can lead to muscle degeneration and can adversely affect its ability to contract with sufficient force. Skeletal muscle typically requires a pre-load stretching in order to contract with sufficient force. In order to sufficiently pre-load stretch the skeletal muscle wrap, the heart has to be expanded, sometime to levels or positions that are unhealthy, or may even cause heart failure. This risk can be especially present during the end diastolic phase when the chambers of the heart are still filling with blood. Chronic overexpansion of the heart can lead to ischemic disease. Additionally, contraction of the skeletal muscle wrap is not generally sufficient if it occurs every heart beat, and greatest efficiency occurs usually with every second or third heart beat stimulation. Futhermore, a single muscle generally cannot provide sufficient contraction (e.g., pumping force) to meet full cardiac stroke requirements for the circulation of blood even for supported beats. As such, even after a skeletal wrap has been reconditioned, as mentioned above it can usually only generate enough pumping force to augment the heart's naturally occurring pumping action and thus, usually cannot replace the pumping action of the heart.

Another approach has been to either replace the existing natural heart in a patient with an artificial heart or a ventricular assist device, or to affix a pump-like device in and/or around the existing natural heart. These circulatory assist devices must be powered by a source, which can be external to the body. External power sources are not typically restrained by size, and sometimes can be large, cumbersome, and/or bulky, which can decrease a patient's mobility and or limit the recipient's lifestyle choices. This can be the case even when a portable system is used for a short period of time. Some power sources, which are external to the body, power or actuate the internal device via cables, electrical cords and/or pneumatic hoses. Indefinitely having percutaneous connectors, which break or perforate through the skin, can enhance the onset of infections, even with meticulous entry site care.

A circulatory assist device can be powered by electrical power that is transmitted to the circulatory assist device using a transformer to transmit power transcutaneously through the skin. Such a power delivery system also can have drawbacks. Power to the circulatory assist device can be interrupted if for example, the coils of the transformer become displaced from each other. Also, electrical conductors can also increase the possibility of cross coupling, which can lead to power disruption because of a diversion of the magnetic flux. Drawbacks on powering and delivering power to these circulatory assist devices have generally limited use of these devices to applications having too brief a time period to, in themselves, provide a real lasting benefit to the recipient.

Others have suggested leaving skeletal muscle in situ and using it to power a circulatory assist device by delivering a force, due to unidirectional or linear shortening of the muscle's myofibers by a linkage, such as a rod, cable, suture or cord having a plurality of bundled or braided fibers along its entire length, these transversing the muscle or its tendon. However, repeated and indefinite transmission of contractible force from muscle to an artificial device using such a linkage presents difficulties which have not been addressed previously. Due to repeated use, the suture would deliver significant pressure to the linkage/muscle interface. For example, the distribution of a muscles typical contractile force directly over half of its cross section would generate compressive stress of nearly 2000 mm of mercury (40 pounds per square inch), reducing or obliterating blood supply to the tissue. Distribution of force into a tendon, with a smaller cross section, would effect even more pressure on the tendon tissue, which already has a reduced blood supply. Chronic repetition of such high pressure may likely harm tissue integrity by causing tissue death or necrosis. Also, the suture would likely reposition itself closer to the distal end of the muscle since the muscle will likely remodel around the suture repeatedly due to the high pressure. As such, a sufficient bond between the suture and muscle to sustain muscle contract force may not develop. This failure to establish the bond and the deteriorating condition may eventually lead to the suture becoming unattached from the muscle and failing.

As can be seen, currently available treatments, procedures, and devices for coupling a prosthetic device to a muscle as a power source to maintain blood circulation have a number of shortcomings that contribute to the complexity of the procedure or device. The current devices and procedures are in limited supply, can be extremely invasive, and may only provide a benefit for a brief period of time. A need exists in the industry for an artificial coupling that can be used to harness the force and power of skeletal muscle in situ whereby an artificial circulation support device can be powered (e.g., pumped or otherwise mechanically actuated) repeatedly and indefinitely.

SUMMARY OF THE PRESENT INVENTION

It is the object of the present invention to provide a device and method for coupling skeletal muscle to prosthetic device that addresses and overcomes the above-mentioned problems and shortcomings in the thoracic medicine art.

Another object of the present invention is to provide a device and method for coupling skeletal muscle to a prosthetic device or bone that minimizes muscle dissection and maximizes the linear force potential of skeletal muscle.

Yet another object of the present invention is to provide a device and method for coupling skeletal muscle to a prosthetic device or bone that leaves the skeletal muscle generally in situ.

Still another object of the present invention is to provide a device and method for coupling skeletal muscle to a prosthetic device or bone that eliminates the need for an external power supply.

It is another object of the present invention is to provide a device and method for coupling skeletal muscle to a prosthetic device or bone that can harness and utilize more than one muscle group synchronously and/or sequentially.

Yet another object of the present invention is to provide a device and method for coupling skeletal muscle to a prosthetic device that can provide a selectable contraction rate for the heart.

A further object of the present invention is to provide a device and method for coupling skeletal muscle to a prosthetic device that can provide independent control of the duration of muscle contraction and the blood ejection from the heart.

It is yet another object of the present invention is to provide a device and method for coupling skeletal muscle to a prosthetic device or bone that is durable and can repeatedly provide for the transmission of contractile force from skeletal muscle to a prosthetic device over an extended time period.

Another object of the present invention is to provide a device and method for use with a circulatory assist device that is free from an external energy source.

Still a further object of the present invention is to provide a device and method for coupling skeletal muscle to a prosthetic device that can provide for independent control of skeletal muscle pre-load and end diastolic pressure of the heart.

Additional objects, advantages, and other features of the present invention will be set forth and will become apparent to those skilled in the art upon examination of the following, or may be learned with practice of the invention.

To achieve the foregoing and other objects, and in accordance with the purpose herein, the present invention comprises a prosthetic coupling for use with skeletal muscle. The strand of the coupling includes a plurality (greater than 5,000) of continuous longitudinally extending filaments, such as polyester fiber, forming a strand. The strand has a first portion that includes a core portion wherein the filaments extend generally parallel to each other, and an exterior portion wherein the filaments are braided along its longitudinal axis around the core portion. The strand also includes a second portion wherein the filaments are generally randomly oriented and organized for integration into skeletal muscle. Preferably, the length of the filaments of the second portion is greater than about 40 mm.

A non-adhering sheath, preferably made from polyurethane, for covering a portion of the strand can also be provided. The sheath can include a tubular shaped portion for covering part or all of the first portion, and a generally frustoconically shaped portion configured for covering the terminal end or distal portion of the muscle where the second portion has been embedded.

A junctional device can be provided adjacent the end of the first portion for assisting in linking or connecting the coupling to a circulatory assist device, such as an artificial heart. An insertion kit for positioning a plurality of filaments into muscle, comprising at least one holder that configured for being attached to an end portion of the muscle, and a guide for conforming the muscle to a desired shape. Furthermore, the insertion kit may also include a frame. In the present invention, the holder may include a prosthetic strip configured for attachment to the end portion of a muscle, or alternatively, a row of teeth configured for grasping the muscle. In yet another alternative embodiment, the holder may include a clamp in which a first portion and a second portion are selectively movable between an open position arid a closed position. The clamp may also include one or more serrated surfaces, or at least one soft surface, and/or taper point penetrating pins.

The insertion kit, as mentioned above, can also include a guide. The guide can include a plurality of bars, or a plate(s). The guide also may include an attachment assembly for assisting in holding the plates against the muscle in compression. A Cushion may also be provided with the plates. Plate also may include a zone wherein a pressure differential is provided to support the muscle on the plate.

An insertion kit of the present invention may also include an inserter for inserting the plurality of filaments into the muscle. The inserter can include a first portion having plurality of slots, such as longitudinally extending slot, wherein each slot being configured to receive a needle. The slots are generally parallel to each other. The inserter may be connected to a frame along with the holder, and the guide. A frame used with the present invention can include a first and second oppositely disposed supports, and the inner surface of each support includes a longitudinally extending groove, whereby the inserter is selectively slidably along the grooves.

The inserter may also include a retainer to secure the needles in the slots.

In an alternative embodiment, the inserter may include a bar having a first portion and a second portion, and creased seam between the first and second portion. The bar may further include a plurality of slots configured for receiving the needles. The needles may even be embedded in the bar.

In yet another alternative embodiment of the present invention, the inserter can include a needle advancer operable to advance needles along the slots, such as one or more rollers, a pneumatic needle advancer, or a spring-loaded needle advancer.

Needles are preferably attached to the plurality of filaments and used to insert the filaments into the muscle. In one embodiment, the needle may include a detachable fin. Also, the needle may include at least one indentation.

In use, the muscle is generally prepared for attachment to the prosthetic coupling having filaments. The muscle can be detached from its attachment at one end, and is positioned in a tensed condition. In one embodiment, the muscle is first detached, and then the filaments are embedded therein. The filaments, preferably in a plurality of tows, of the prosthetic device are embedded in the muscle. Needles can be connected to the tows, and can be advanced into the muscle either all at once, or in a group of less than all.

The filaments of the second portion are embedded into the muscle at or adjacent one of its ends, preferably the terminal or distal end. Preferably the filaments are gathered into a plurality of tows. Each tow is swagged into or otherwise connected to a needle, and sewn into the muscle. The tows can be sewn through the muscle obliquely at least two, and preferably three times, in a S-shaped pattern. A sheath is unfolded to cover a portion of the strand, including the sites where the filaments enter the muscle, and the sites where the filaments are exposed at the surface of the muscle. The muscle covering portion of the sheath is generally diagonally corrugated to ensure against buckling as the muscle shortens and thickens with contraction.

BRIEF DESCRIPTION OF THE DRAWINGS

While the specification concludes with claims particularly pointing out and distinctly claiming the present invention, it is believed the same will be better understood front the following description taken in conjunction with the accompanied drawings in which:

FIG. 2 is longitudinal sectional view of a prosthetic coupling made in accordance with the present invention;

FIG. 3 is cross sectional view of the prosthetic coupling taken along line 3—3 in FIG. 2;

FIG. 16 is a perspective view of an exemplary holder and guide positioned in a frame made in accordance with the present invention;

FIG. 19A is a perspective view of an alternative embodiment of an inserter made in accordance with the present invention;

FIG. 21A is a perspective view of another alternative embodiment of a needle made in accordance with the present invention;

FIG. 21B is a perspective view of the needle of FIG. 21A in an inserter made in accordance with the present invention;

FIG. 23, is a partial cross-sectional view of an alternative embodiment of an inserter made in accordance with the present invention;

DETAILED DESCRIPTION OF THE INVENTION

Figure 1:
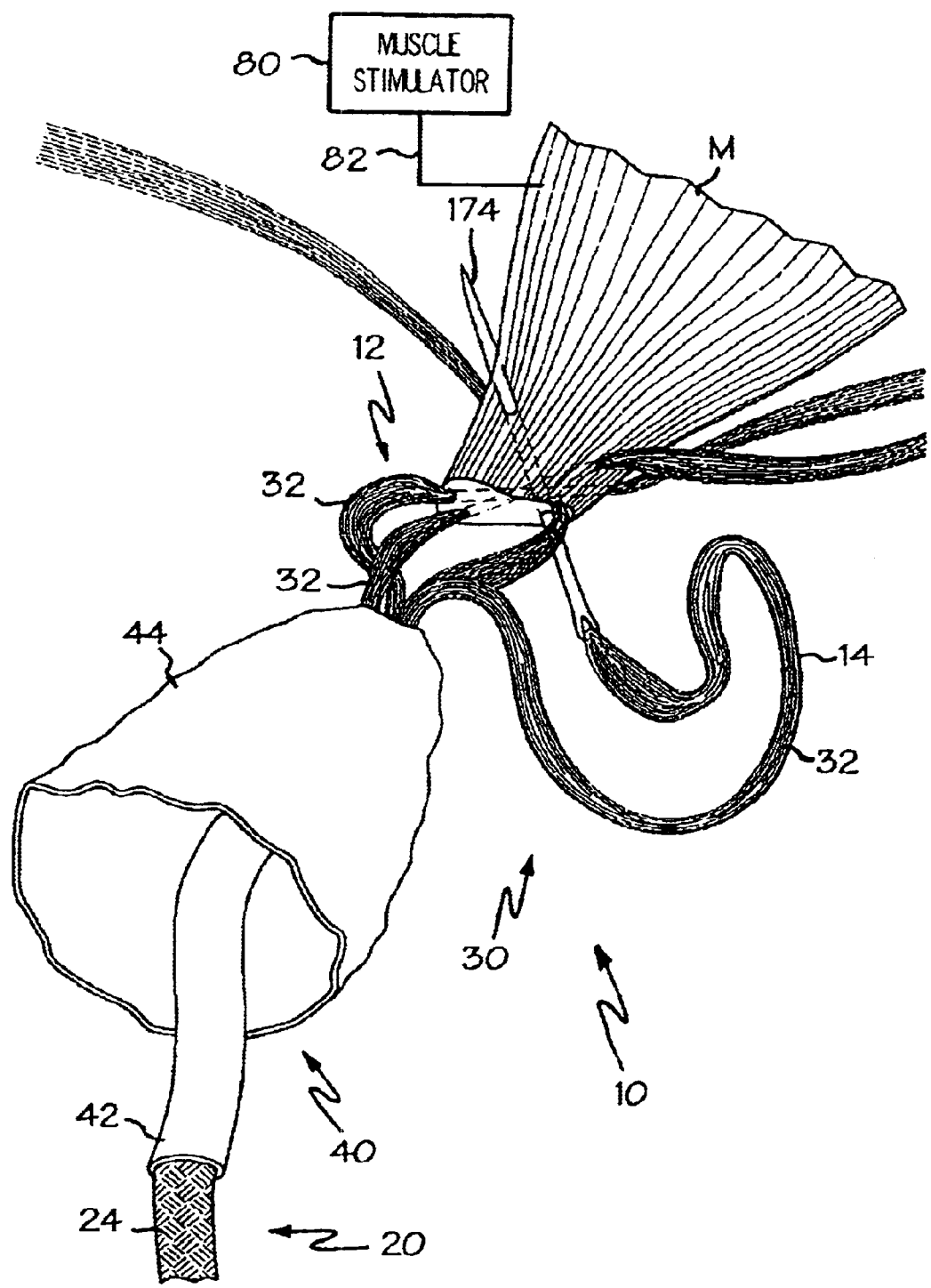
FIG. 1 is perspective view of the prosthetic coupling made in accordance with the present invention being attached to the distal end of skeletal muscle.

Referring now to the figures in detail wherein like numerals indicate the same elements throughout the views, the present invention includes a prosthetic coupling generally identified as 10 for utilizing skeletal muscle, preferably left generally in situ, to power or actuate a circulatory assist device, such as an artificial heart. Prosthetic coupling 10 can include a strand 12 or suture, which can have thousands of fine individual filaments 14 or fibers, for repeatedly and indefinitely transmitting the contractile force of muscle M, and preferably skeletal muscle, to a prosthetic device (see, e.g., PD in FIG. 2). The filaments 14 used with the present invention should be configured so that removal of the filament 14 from the muscle M, once embedded, is not easy accomplished. Also, the filament 14 of the present invention preferably should be capable integrating or of forming a bond with the muscle M to sustain the force caused by linear shortening of the muscle M, which can be greater than 40 N, and in some cases greater than 80 N. The filaments 14 should be configured to assist in maximizing the potential surface area of the strand 12, which thereby enhances tissue integration into and around the filaments 14, as will be detailed below and also can permit the transfer of increased power via prosthetic coupling 10. To increase the surface area of the strand 12, the filaments 14 should have a sufficiently small diameter, such as about 12 µm. In an alternative embodiment, each filament 14 can have a diameter of less than about 40 microns, and preferably less than about 10 microns.

Filaments 14 are preferably made of a material that does not dissolve when placed in the body over time and can withstand lateral compressive and shear forces applied by muscle M as it contracts, and thus, moves the embedded filaments (e.g., 14). The material of the filament 14 should also have a coefficient of friction to assist in preventing the filaments 14 from becoming unembedded in or detached from the muscle M and thus, removed. Preferred materials of the filament 14 may also be porous or textured to further increase the coefficient of friction, enlarge the surface area of filament 14, and/or enhance tissue integration in and around the filament 14 whereby the filament 14 is not easily removed from the muscle M. Illustrative examples of materials which may be suitable for use as filaments 14 in the present invention include bulk polymers such as, polyolefins (e.g., polyethylenes, such as high molecular weight polyethylenes, or very high molecular weight linearly crystalline polyethylenes (e.g., the brand name SPETRA), polypropylenes, such very high molecular weight polypropylenes), polytetrafluroethylene (PTFE), polyester, and the like.

The prosthetic coupling 10 of the present invention has at least two portions, a first or prosthetic attachment portion 20, and a second or muscle coupling portion 30. The filaments 14 are generally continuous throughout both portions 20 and 30, respectively, and are generally organized differently in the prosthetic attachment portion 20 from the muscle coupling portion 30 for use in the present invention.

Turning now to FIG. 3, the filaments 14 are preferably configured and organized in prosthetic attachment portion 20 so as to assist in attaching the prosthetic coupling 10 to a prosthetic device PD, such as a circulatory assist device. The organization and configuration of the prosthetic attachment portion 20 should assist in reducing the extensibility and/or elastic nature of the strand 12, and thus, minimizing the energy dissipation along the length of strand 12. Preferably, the prosthetic attachment portion 20 should be extendable only about 1% to 2% of its overall length when subjected to the expected force. A kemmantel-type or compact cord-like structure can be used as prosthetic attachment portion 20 to assist in efficiently transmitting longitudinal contraction forces from a muscle M, or group of muscles, to a bone or prosthetic device PD.

Turning now to FIG. 3, the prosthetic attachment portion 20 preferably includes a core portion 22 and outer filaments 24. Core portion 22 can have a plurality of filaments 14 bundled and extending generally parallel to each along the length of the prosthetic coupling 10. The outer filaments 24 can be organized to provide mechanical stability and structural integrity to the first or prosthetic attachment portion 20. For example, the outer filaments 24 can be gathered into several groups or bundles 26, and then braided around the core portion 22 to provide a jacket around the core portion 22. In one embodiments about 40 percent, and preferably about 10 percent, of all the filaments 14 can be gathered into several, such from about 8 to about 16, small bundles 26 and braided around the core portion 22 to provide the desired kemmantel-type cord structure preferred for use with the present invention.

As exemplified in FIG. 2, the distal portion 28 of the prosthetic attachment portion 20 can be provided with a junction device 50, such as a connector, clamp, or other mechanical linkage, configured to assist in connecting or coupling the coupling 10 to mechanical linkages 60 (e.g., hydraulic cylinders and pistons, sheathed cables, pulleys and the like) of the prosthetic device, such as the circulatory assist device PD. The prosthetic device should provide assistance in the maintenance of blood flow and circulation though a body's circulation system. Illustrative examples of circulatory assist devices that may be suitable for use with the present invention can include an intraventricular pump, such as the device disclosed in U.S. Pat. No. 5,139,517 (Corral), an artificial heart that entirely replaces that existing natural heart, such as the device disclosed in U.S. Pat. No. 4,904,225 (Chareie, et al.), a cardiac assist device used with the natural heart, such as the device that is discloses in U.S. Pat. No. 2,826,193 (Vineberg), U.S. Pat. No. 3,455,298 (Anstadt) and/or U.S. Pat. No. 4,536,893 (Parravicini), a ventricular assist device, such as the device disclosed in U.S. Pat. No. 4,690,134 (Snyders), and/or a heart harness pump, such as the devices disclosed in U.S. Pat. No. 5,957,977 (Melvin), the disclosures of which are hereby incorporated herein by reference. Preferably, the prosthetic devices should also be configured to assist in maintaining the force developed by the muscle's M contraction throughout the ejection stroke of the prosthetic device PD without additional metabolic demands on the muscle M, such as skeletal muscle. Illustrated examples of such devices suitable for use with a prosthetic device PD can include ratches, valves, and the like.

The second or muscle coupling portion 30 of the coupling 10 is provided generally so as to assist with integration into and/or maintenance of the filaments 14 within the muscle tissue M. Muscle coupling portion 30 preferably can include a plurality of generally unbraided, unspun, untwisted and unplaited filaments 14 for maximizing the surface area of the strand 12 of the muscle coupling portion 30. Filaments 14 of the muscle coupling portion 30 should have a length sufficient so they can be dispersed within the distal or terminal portion of the muscle M so that the muscle's contraction generates low pressure on the filaments 14. Also, the length, and thus its overall surface area, of filaments 14 should be such that the sum of any shear forces on a filament 14 would sustain the required tensile force on the filament 14 in the presence of physiological levels of hydrostatic pressure in the muscle tissue. A suitable filament 14 for use in the muscle coupling portion 30 with the present invention can have a length greater than 40 mm.

The filaments 14 of the second portion 30 are configured so that they can be gathered into a plurality of easily separable tows or bundles 32, and then each tow 32 can be swagged into an instrument for sewing an/or embedding the filaments 14 into the muscle, such as a tapered needle 174 (either straight or curved), or other surgical instrument, which will be discussed below in greater detail.

Figure 4:
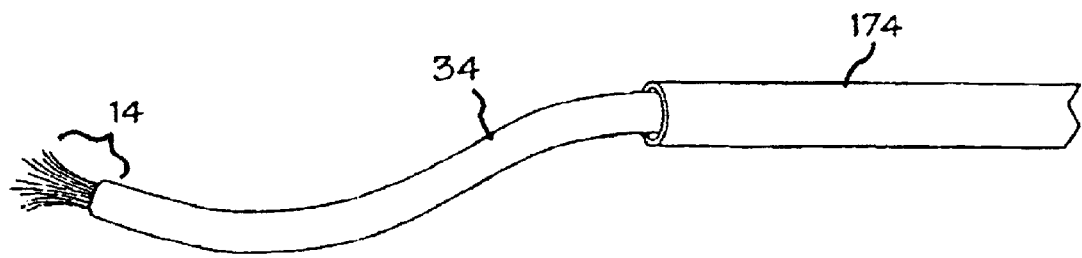
FIG. 4 is a partial enlarged perspective view of alternative embodiment of the prosthetic coupling make in accordance with the present invention.

As exemplified in FIG. 4, the tows 32 of filaments 14 of the muscle coupling portion 30 may be encased in or impregnated with, or both, a cover material 34 to lessen friction between the filaments 14 and the muscle M so that the filaments 14 can be more easily placed in the muscle M, as desired. The cover material 34 should preferably be removable or biodissolvable so not to adversely interfere with filament 14 placement in the muscle M and integration into the muscle M. Illustrative examples of material which might be suitable for use in the present invention as a cover material 34 can include biocompatible gelatin, albumin, other proteins and polysaccharidess, and the like.

Turning back to FIGS. 1 and 2, a sheath or sleeve 40 can be provided over the strand 12 so as to assist in inhibiting fibrous tissue from adhering to the prosthetic coupling 10 and thus, interfering with its function and/or generally linear movement. The sleeve 40 can include a tube-shaped portion 42 that partially or entirely covers, and preferably surrounds or encases, at least a portion of the prosthetic attachment portion 20. It is contemplated that the exterior surface of the prosthetic attachment portion 20, and preferably the outer filaments 24, may be formed from a fiber(s) or material(s) that assists in resisting tissue integration, which can be different from the filaments 14 of the muscle coupling portion 30. The sleeve 40 can also include an invertible generally frustoconically shaped portion 44 that can be positioned or unfolded around the portion of the muscle M in which the second portion 30 is embedded. The generally frustoconically shaped portion 44 preferably has a generally diagonal corrugated configuration so as to assist in allowing for radial and/or axial expansion and contraction of the muscle M as it contracts and relaxes. Illustrative examples of material which may be employed as sleeve 40 of the present invention can include polyurethane, such as that provided under the brand name TECOFLEX by Thernniocardio Systems of Woburn, Mass.

Figure 5:
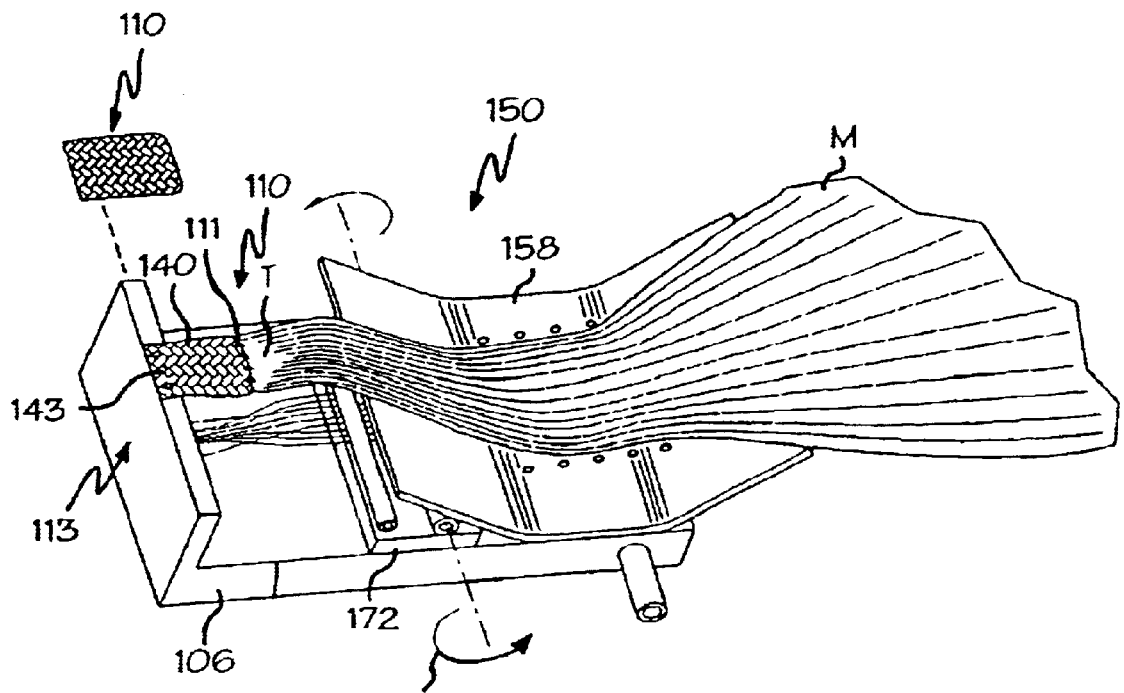
FIG. 5 is a perspective view of an insertion kit made in accordance with the present invention and illustrating an exemplary arrangement for insertion of filaments into muscle.

To assist in inserting the prosthetic coupling 10 in the muscle M, an insertion kit 102 may be used. As exemplified in FIG. 5, the insertion kit of the present invention is illustrated as having a holder 110 and guide 150 each for the muscle M, and preferably an inserter 172. Each of these features and assemblies will be explained in greater detail below.

Holder 110 of the present invention assists in stabilizing and positioning the muscle M, and preferably an end portion of the muscle M, for insertion of filaments 14 into the muscle M in a plurality of tows 32. Holder 110 should further assist in enhancing desired distribution of the filaments 14 in the muscle M (e.g., separated from each other and/or not intersecting). Holder 110 is generally adapted and configured for holding a part of the muscle M, and preferably an end portion of the muscle M or tendon(s) T, so that tensile stress is applied to the fibers in the muscle M to assist in controlling the orientation of the fibers in the muscle M as the filaments 14 are being inserted. One end 111 of the holder 110 is generally attached to the end portion of the muscle M or a tendon T. Another end 113 of the holder 110 is generally attached to a structure, such as a frame 106 or other stabilizing device, so that tensile stress is applied to the muscle M along its length. One or more holders may be utilized to hold a particular muscle or part of the muscle M.

Figure 6:
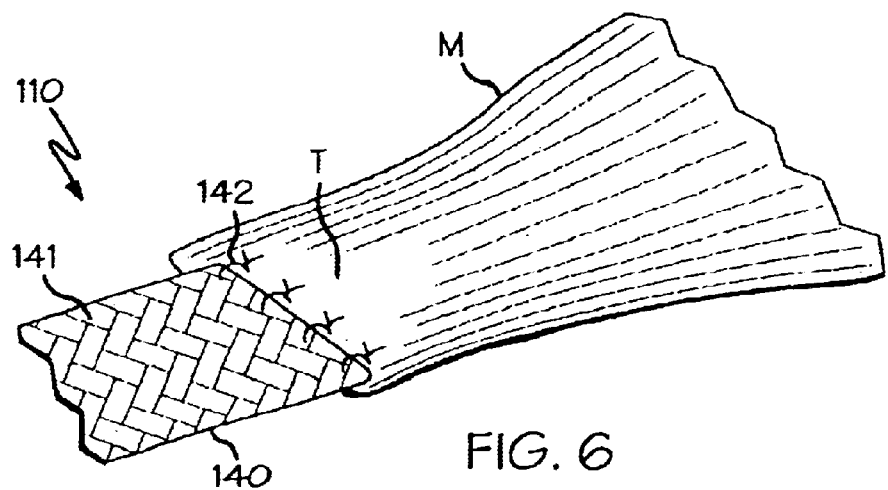
FIG. 6 is an enlarged perspective view of a holder made in accordance with the teachings of the present invention that is attached to a muscle.

One embodiment of a holder 110 is exemplified in FIG. 6. Holder 110 can include a fabric or other suitable strip 140. One end 141 of the strip 140 is preferably configured so that it can be attached to the end portion of the muscle M or tendon T, preferably using one or more standard sutures 142. The other end 143 of the strip 140 (shown in FIG. 6) can be attached to a frame 106 or another support structure. Strip 140 should be sufficient strong so that the material does not stretch or tear in use with tensile stress is being applied to the muscle M. While it is desirable that the material 140 be biocompatible, such a requirement is not necessary as the holder 110 is not inserted into the body. Illustrative examples of materials that could be suitable for use as strip 140 with the present invention include polyester weave or expanded PTFE.

Figure 7:
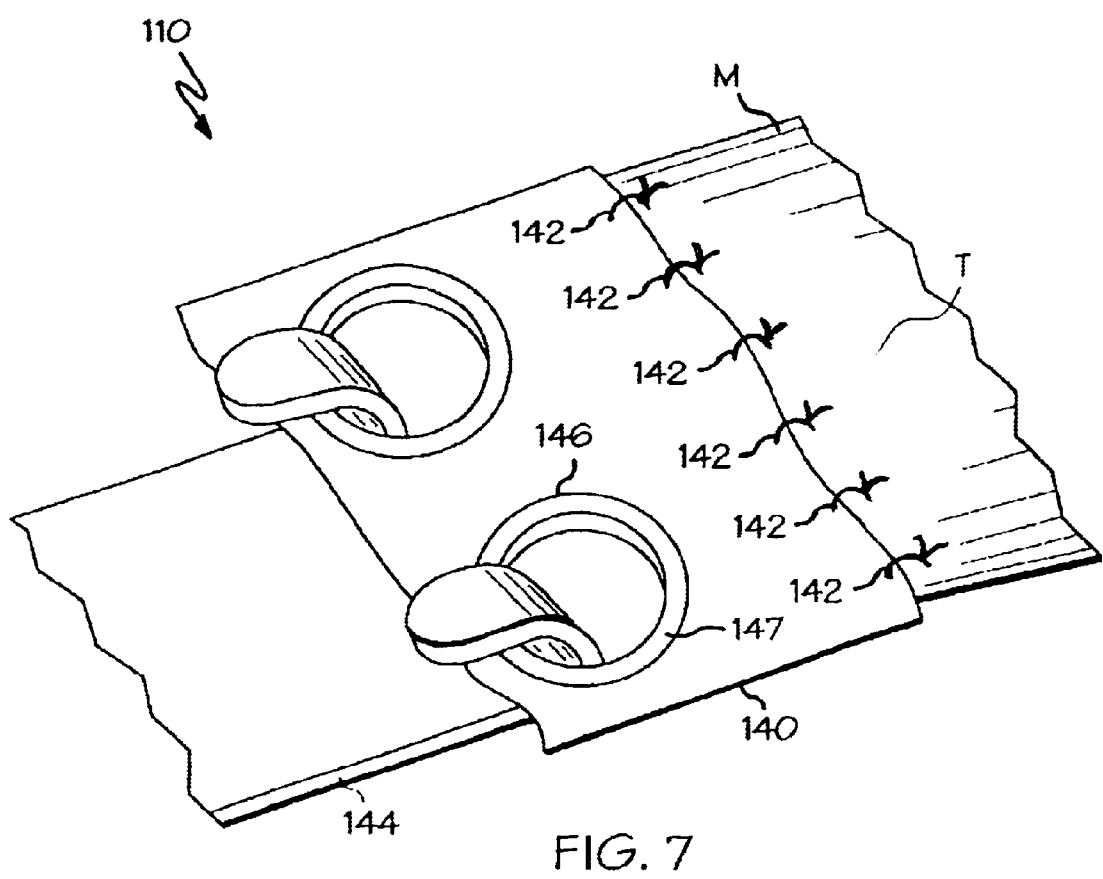
FIG. 7 is an enlarged perspective view of an alternative view of a holder made in accordance with the teachings of the present invention that is attached to a muscle.

In an alternative embodiment, strip 140 may include one or more openings or apertures 146, as exemplified in FIG. 7. In such an embodiment, the other end 143 of the strip 140 can be hooked or otherwise secured to a retractor 144 or other stabilizing bar or surgical instrument that can be manually held, or can be attached to a frame (e.g., 106) or other support structure. Rings or other support or stabilizing structures 147 may be used in openings 146 to assist in maintaining the structural integrity of the material of strip 140, in use.

Figure 8A:
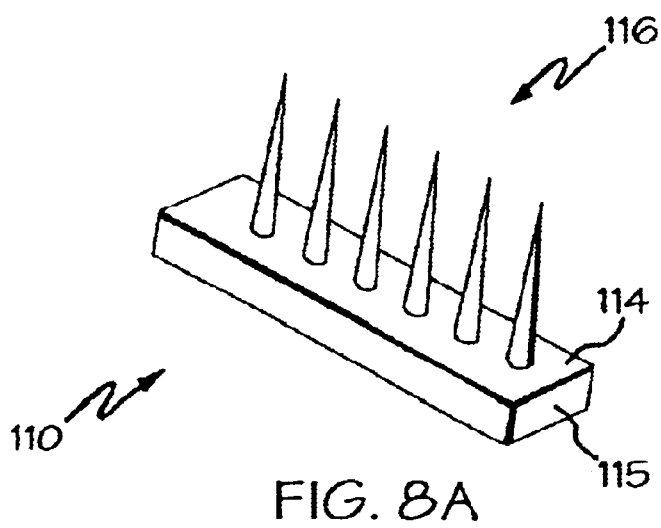
FIG. 8A is a perspective view of yet another alterative embodiment of a holder made in accordance with the teachings of the present invention.
Figure 8B:
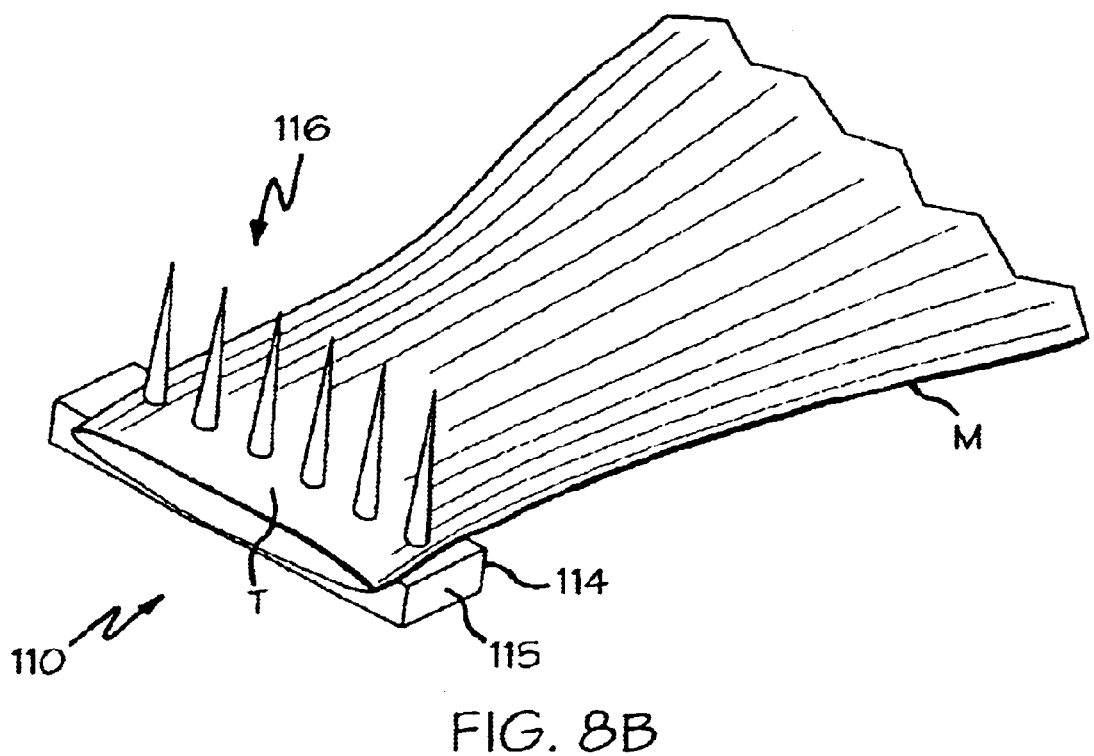
FIG. 8B is a perspective view of the holder illustrated in FIG. 8A where the muscle in connected to the holder.

FIGS. 8A and 8B exemplify yet another alternative embodiment of a holder 110 used with the present invention. A rake-like structure 114 can be used to assist in applying tensile stress to the muscle M., and can include a plurality of teeth 116 that preferably can extend away from a base 115. The teeth 116 are each generally configured so that the muscle M or tendon T can be impaled thereon, as exemplified in FIG. 8B, such as with a tapered point configuration. Base portion 115 can be attachable to a support structure, such as frame 106, as illustrated in FIG. 16.

Figure 9A:
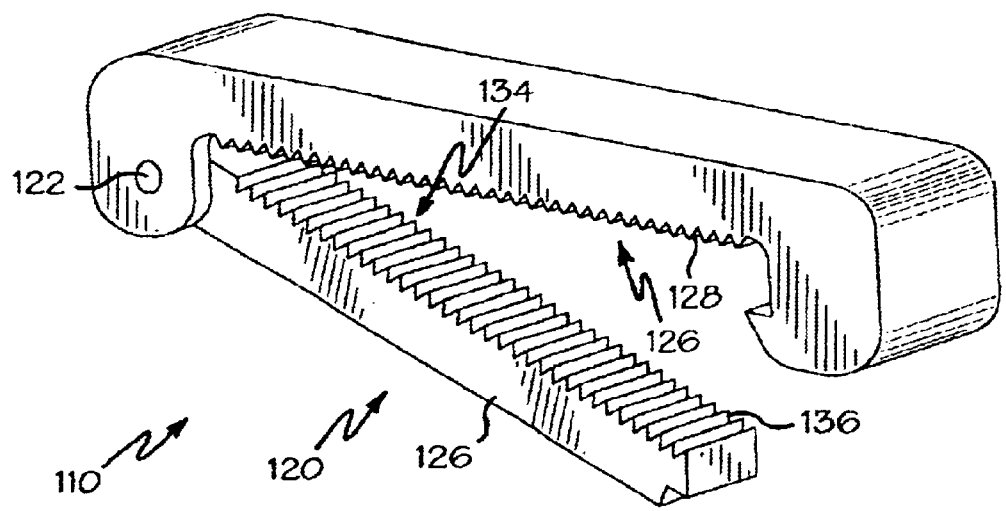
FIG. 9A is a perspective view of another alterative embodiment of a holder made in accordance with the present invention in an open position.
Figure 9B:
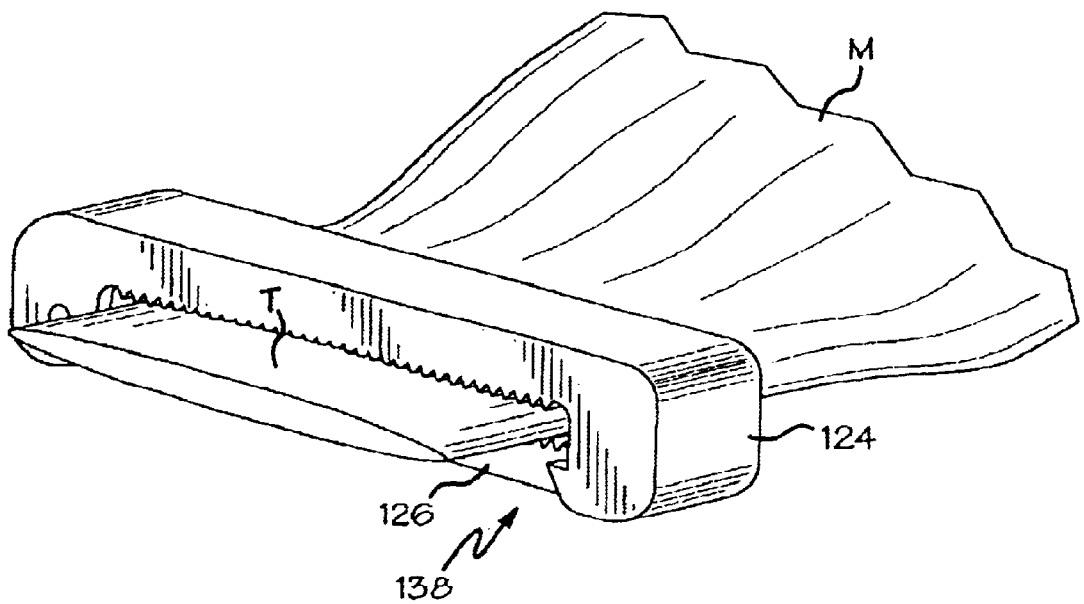
FIG. 9B is a perspective view of the holder of FIG. 9A illustrating a muscle inserted into the holder in a closed position.

FIGS. 9A and 9B also exemplify yet another embodiment of a holder 110 that can be used with the present invention. A clamp 120 can also be used as holder 110 to apply tensile stress to the muscle M for insertion of the filaments 14. Clamp 120 should have a first portion 124 and a second portion 132 that can be selectively movable between at least an open position (see, e.g., FIG. 9A) and a closed position (see, e.g., FIG. 9B) so that the end portion of the muscle M and/or the tendon T is insertable therein. The first portion 124 is illustrated as being movable relative to the second portion 132 on a pivot joint or hinge 122. The clamp 120 can assist in holding the muscle M and/or tendon T by having inner surfaces 126 and 134, respectively, be configured and adapted for compressively engaging an end portion of the muscle M or the tendon or tendons T. As exemplified in FIGS. 9A and 9B, the inner surface 126, inner surface 134, or both, may have a serrated surfaces (see., e.g., serrated surfaces 128 and 136, respectively) to assist in grasping and holding the muscle M or tendon T. Clamp 120 can be secured in a closed position using various techniques known in the industry including but not limited to screw secured, ratchet secured 138, or other locking or securing devices known in the industry.

Holder 110 also may be configured to hold the muscle M at a position proximal to the tendon T or end portion of the muscle M, as previously illustrated and discussed. An alternative embodiment of a clamp 220 is exemplified in FIG. 10, which can include a cushion 229, a cushion 234, or both, on first and second portions 224 and 232, respectively. Clamp 220 is configured to selectively and compressively engage a portion of the muscle M, and preferably the belly of the muscle M.

The inserter kit 102 of the present invention also may include a guide 150 for assisting in conforming one or more surfaces of the muscle M to a pre-determined shape and/or location, which can assist in insertion of the filaments 14 into the muscle M. Guide 150 preferably assists in physically restraining the muscle M in a taut or tensed condition. Guide 150 is generally positioned in the inserter kit 102 such that it is away from, and preferably laterally away from, the holder 110, as exemplified in FIGS. 5 and 16.

Figure 11A:
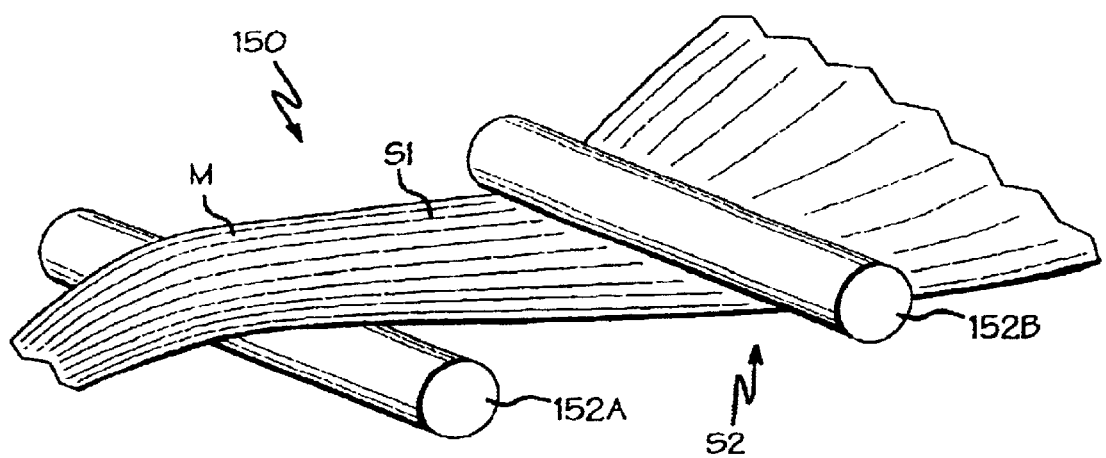
FIG. 11A is a perspective view of a guide made in accordance with the present invention.
Figure 11B:
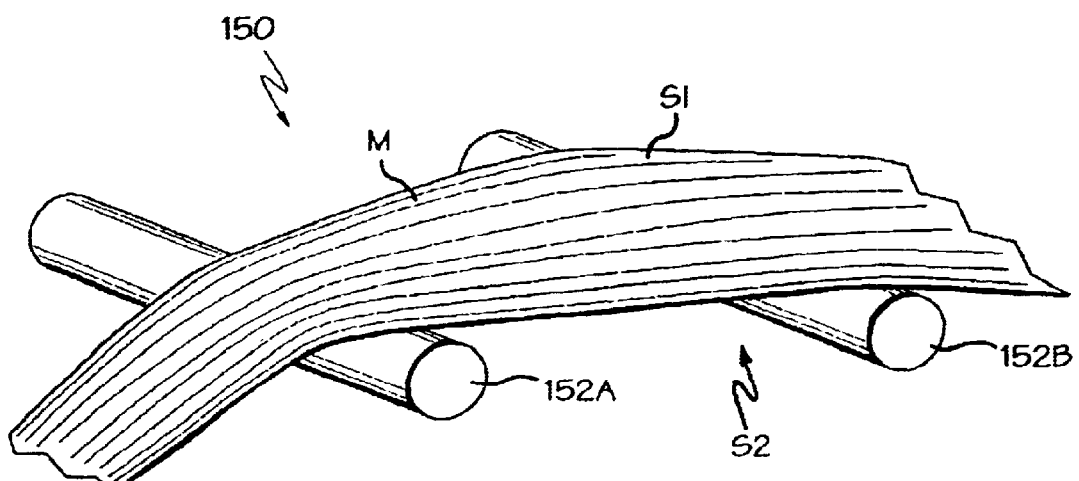
FIG. 11B is a perspective view of the guide of FIG. 11A whereby the muscle is positioned differently than in FIG. 11A.

Turning now to FIGS. 11A and 11B, guide 150 may include one or more bars 152. Preferably, bars 152 are generally cylindrically shaped or otherwise shaped and configured so as to assist in minimizing trauma to the muscle M during insertion of filaments 14. Bar 152 can be used with the present invention having alternative cross sectional configurations, including square, parallelogram, triangular, oval and the like. When more than one bar 152 is used as guide 150 (e.g., 152A and 152B), they are preferably spaced apart, and laterally apart, from each other. Bars 152A and 152B can be positioned such that opposites surfaces (see, e.g., S1 and S2) of the muscle M are in contact with the bars 152A and 152B (see, e.g., FIG. 11A), or such that the same surface(see, e.g., S2) of the muscle M is in contact with the bars 152A and 152B (see, e.g., FIG. 11B).

As exemplified in FIG. 16, the bar or bars 152 are generally positioned across the insertion kit 102 along a transverse axis, and supported by frame 106 away from the holder 110. It should be noted, and as will be appreciated by those skilled in the art, that any embodiment of the holder 110 can be used with any embodiment of the guide 120.

Figure 12A:
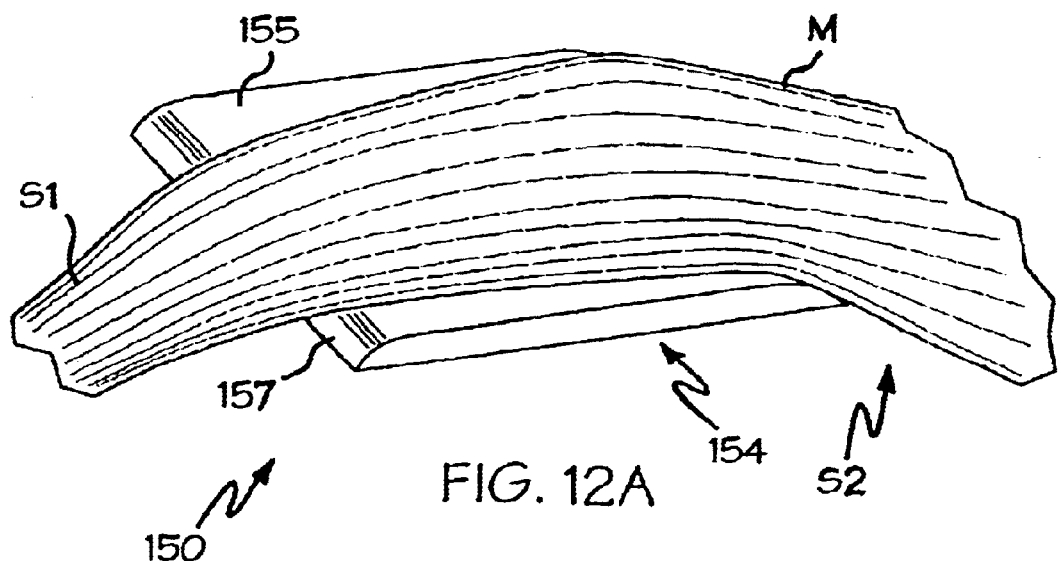
FIG. 12A is a perspective view of an alternative embodiment of a guide made in accordance with the present invention.
Figure 12B:
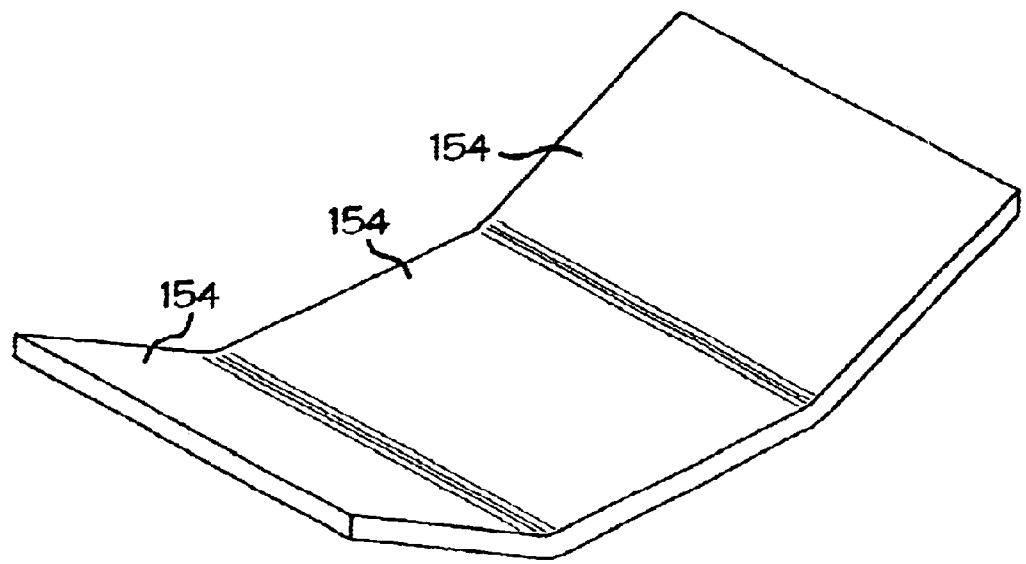
FIG. 12B is a perspective view of another alternative embodiment of a guide made in accordance with the present invention.

FIGS. 12A and 12B, exemplified an alternative embodiment of a guide 150 of the present invention. Guide 150 can be generally one plate (see, e.g., FIG. 12A) or more than one plate 154 (see, e.g., FIG. 12B) each having a generally smooth surface 155 upon which a surface (e.g., S2) of the muscle M can be placed against it. Plate(s) 154 preferably can include generally smooth or rounded longitudinal edges 157 to minimize trauma to the muscle M as it is being stretched or tensed across the guide 150.

Figure 13:
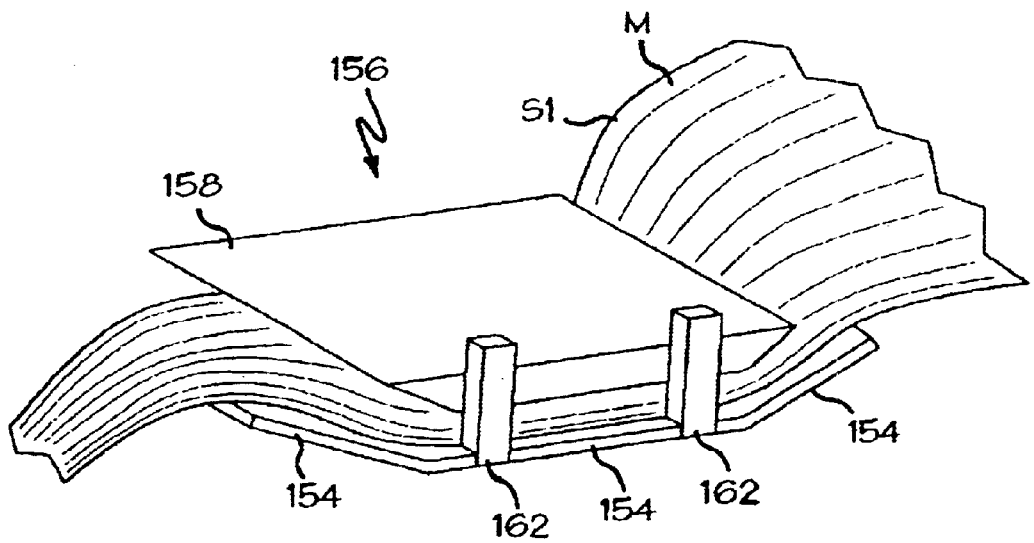
FIG. 13 is a perspective view of an alternative embodiment of the guide including a displacement mechanism.

Guide 150 may also include a displacing mechanism 156, such as is illustrated in FIG. 13, for assisting in having the muscle M contact the guide 150. Displacing mechanism 156 can include a plate 158, which can be releasably connected or secured to the plate 154 using an attachment assembly 162 for assisting in selectively applying compression forces to the muscle M. Attachment assembly 162 can take the form of any suitable assembly that can be used to adjust the compression forces applied to such portion of the muscle M interposed in the guide 150, as desired. Illustrated examples of such attachment assemblies 162 that can be used with the present invention can include a ratchet, or screws assembly.

Figure 14:
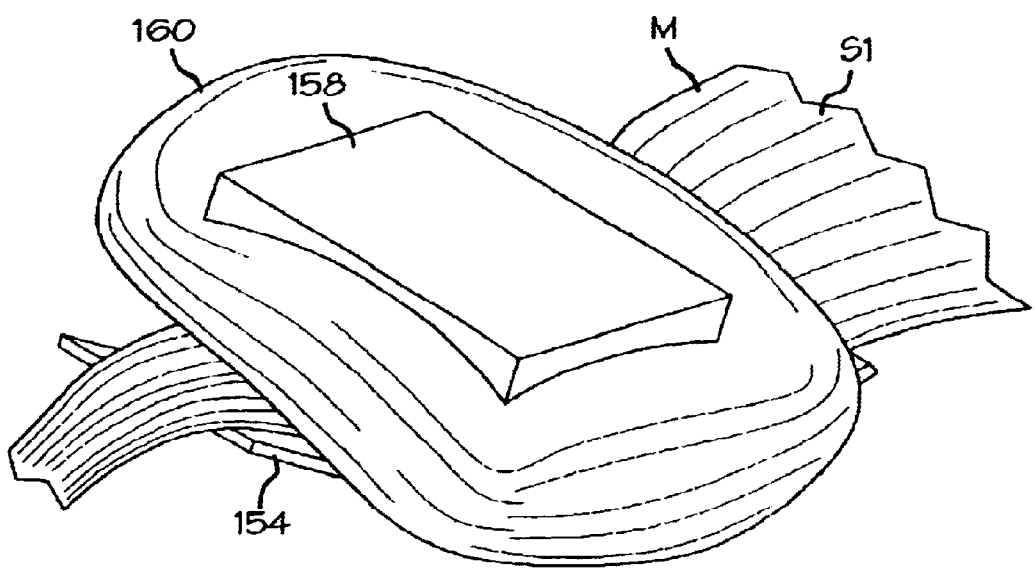
FIG. 14 is a perspective view of the guide of FIG. 13 with an alternative embodiment of a displacement mechanism.

The displacement mechanism 156 used with the present invention may also include a cushion 160, as illustrated in FIG. 14, interposed between the muscle M and the plate 158. Cushion 160 can be provided to assist in applying uniform compression forces to the muscle M. Illustrative examples of cushions that are suitable for use with the present invention can include fluid filled sacs, a foam structure or the like.

Figure 15A:
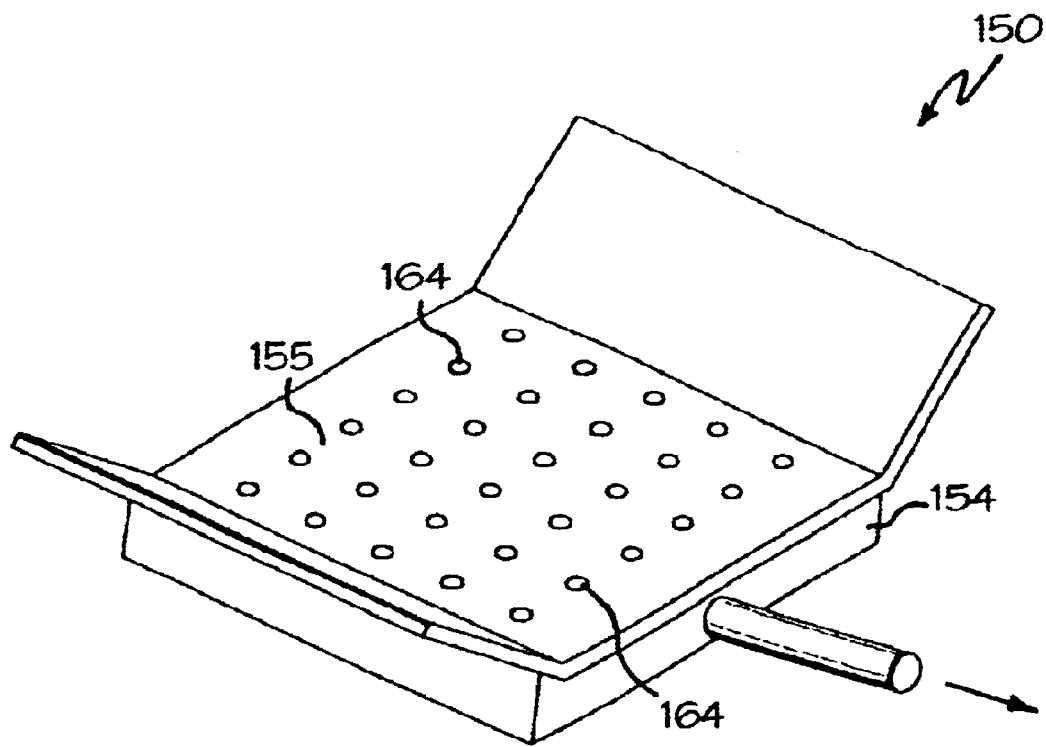
FIG. 15A is a perspective view of an alternative embodiment of the guide made in accordance with the present invention.
Figure 15B:
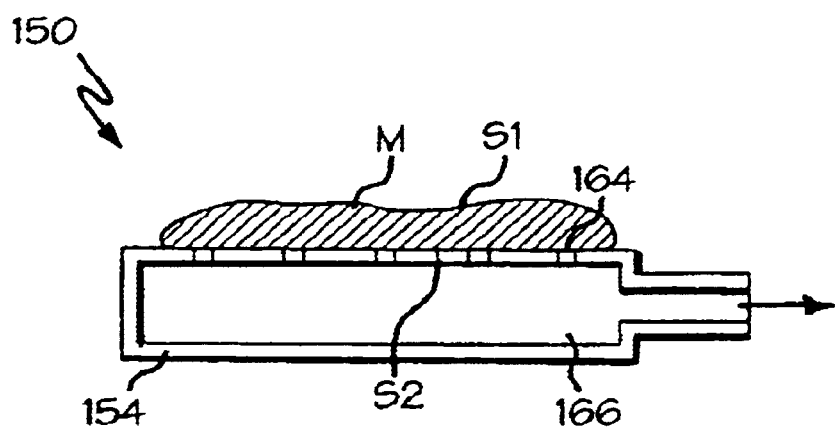
FIG. 15B is a cross-sectional view of the guide of FIG. 15A.

Turning now to FIGS. 15A and 15B, the guide 150 may also include a pressure chamber 166 and the plate 154 can include one or more, and preferably a plurality of pores 164 in fluid communication with the pressure chamber 166 for providing a pressure differential, such as an underpressure and vacuum, on a portion or zone 155 of plate 154. An underpressure force can assist in pulling or holding a portion of muscle M against the surface 155 of plate 154 so that muscle M can be held in a tensed condition.

The present invention also preferably can include an inserter 170 for assisting in implanting one or more, and preferably a plurality of tows 32 of filaments 14 in a muscle M. An inserter 170 preferably will assist in controlling the insertion of the tows 32 using needles 174 or other surgical instrument, which in turn will place the tows 32 and filaments 14 in a predetermined pattern within the muscle M. Inserter 170 will preferably be configured and adapted so that it can be mounted and moved along the frame 106 to assist in inserting the filaments 14 in the muscle M. Alternatively, the inserter 170 can be mounted on the frame 106, and the inserter 170 may be adapted to move or advance the needles 174 into the muscle M. In all subsequent references to propelling all needles 174, it is understood that velocity achieved by varying needles 174 may impart sufficient kinetic energy that needles 174 continue to move in the same path after loss of contact with slot 190, to, through and/or beyond the muscle M.

Figure 17A:
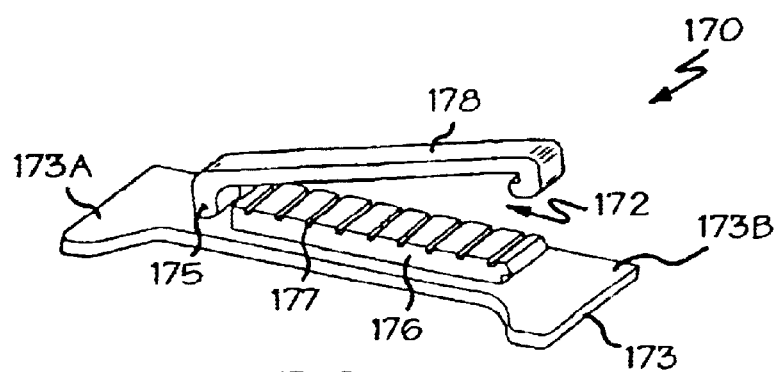
FIG. 17A is a perspective view of an inserter made in accordance with the present invention, in an open position.
Figure 17B:
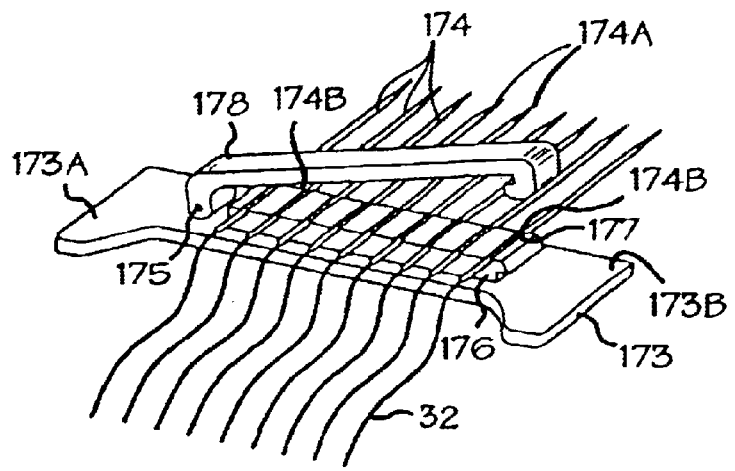
FIG. 17B is a perspective view of the inserter of FIG. 17A with needles positioned in the inserter.
Figure 17C:
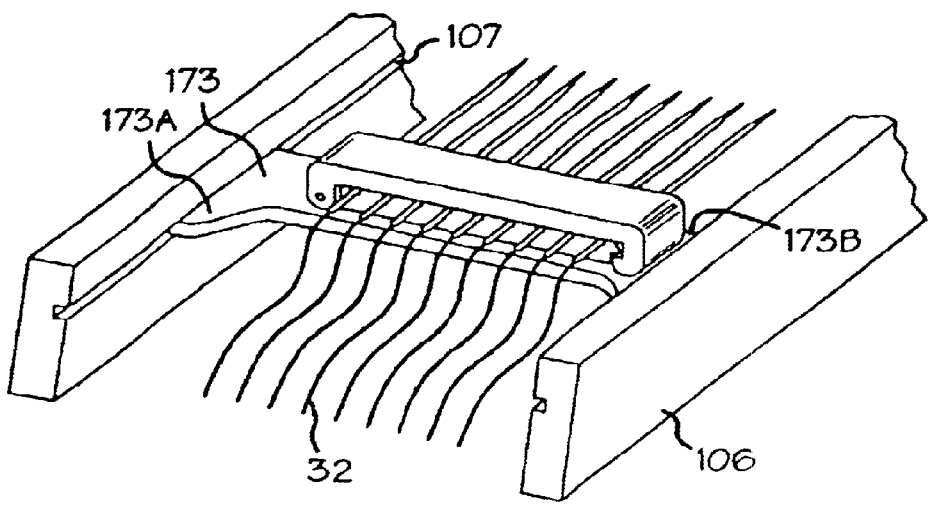
FIG. 17C is a partial enlarged perspective view of the inserter of FIGS. 17A and 17B in a closed position, and positioned in a frame in accordance with the present invention.

FIGS. 17A–C illustrate a clasp 172 that can serve as an inserter 170 with the present invention. Clasp 172 may include a base 173 having one or more notches, slots or grooves 176 configured and adapted for receiving a needle 174, and preferably the proximal portion 174B of the needle 174, in a predetermined pattern or arrangement. To assist in maintaining the needles 174 in the desired orientation and position in grooves 176, the clasp 172 may include a retainer or second portion 178 that can be selectively moved between at least one open position (see, e.g., FIGS. 17A and 17B) and a closed position (see, e.g., FIG. 17C) whereby the clasp may be secured or maintained in the closed position using any suitable apparatus or assembly, such as a ratchet (e.g., 180). In a preferred embodiment, the second portion 178 may be movable relative to the base 173 about a pivot hinge 175.

As exemplified in FIG. 17C, base 173 may also include flange portions 173A and 173B, respectively. Flange portions 173A and 173B are each preferably adapted and configured to be received in a slot 107 in the frame 106, and preferably along the interior surface of the frame 106 so that the inserter 170 (and clamp 172) can be advanced (e.g., slid back and forth along the frame 106) to assist in inserting the needles 174 and the tows 32 into the muscle M.

Figure 18A:
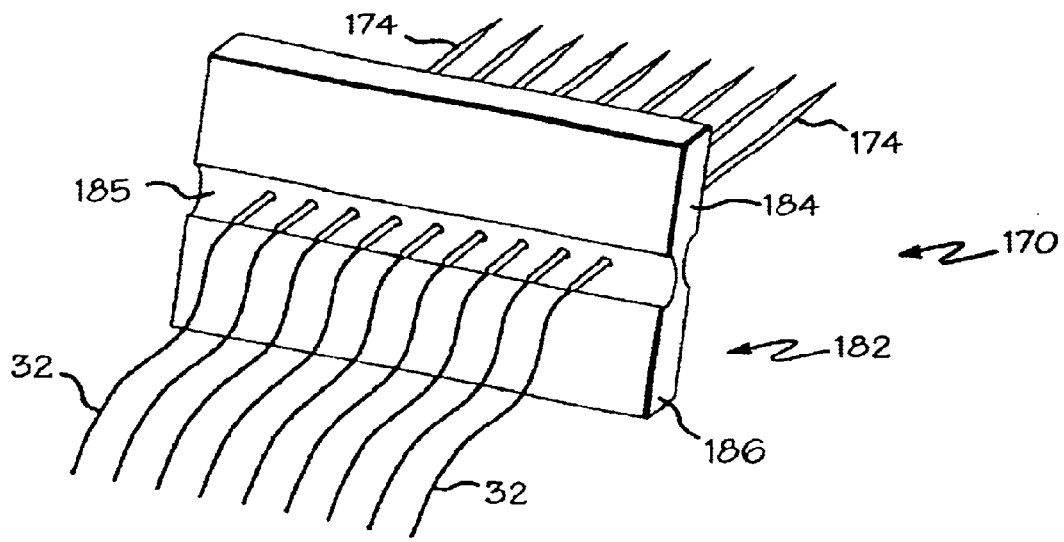
FIG. 18A is a perspective view of an alternative embodiment of an inserter made in accordance with the present invention.
Figure 18B:
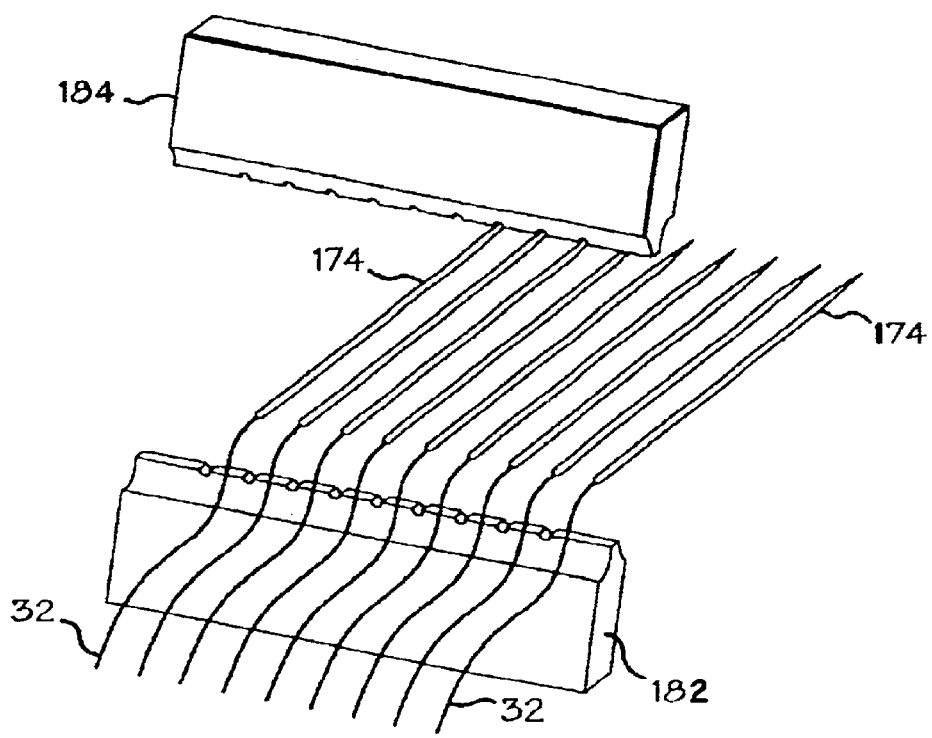
FIG. 18B is a perspective view of the inserter of FIG. 18A once the bar has been broken.

FIGS. 18A and 18B exemplify another embodiment of an inserter 170 in which the needles 174 may be embedded in a bar 180. The bar 180 preferably has a crease 185, is perforated, has a portion of less material or structural weakness, whereby the bar 180 can be broken into first and second portions 184 and 186, respectively, as exemplified in FIG. 18B. Bar 184 is preferably made of a material that will grasp and hold the needles 174, as illustrated in FIG. 18A, so that the inserter 170 can be used to assist in placing tows 32 in the muscle M, but also can be broken to remove the needles 174 from the bar 182, as illustrated in FIG. 18B. Illustrative examples of suitable materials that can be used for bar 182 in the present invention may include ceramics, polymers, and the like.

As mentioned above, inserter 170 can be mounted on the frame 1(06 in the present invention, and the needles 174 can be advanced or propelled relative to the inserter 170 into the muscle M. FIG. 19A exemplifies one embodiment of such an inserter 170. Inserter 170 can include a base 188 having a plurality of tubes, slots or grooves 190 in a predetermined orientation. Slots 190 are preferably oriented parallel to each other to assist in inserting the tows 32 and filaments 14 into the muscle M in a generally parallel orientation. Slots 190 are generally configured and adapted to receive a needle 174 in each of the slots 190 whereby the needle 174 can be selectively and slidably movable along the slots 190, as will be discussed below. Inserter 170 can also include a needle advancer 194 for advancing the needles 174, preferably along slot or groove 190 into the muscle M. Needle advancer 194 can take the form of a roller 195 that is configured to generally mechanically advance or propel the needles 174 in the slots 190 into the muscle M.

Figure 19B:
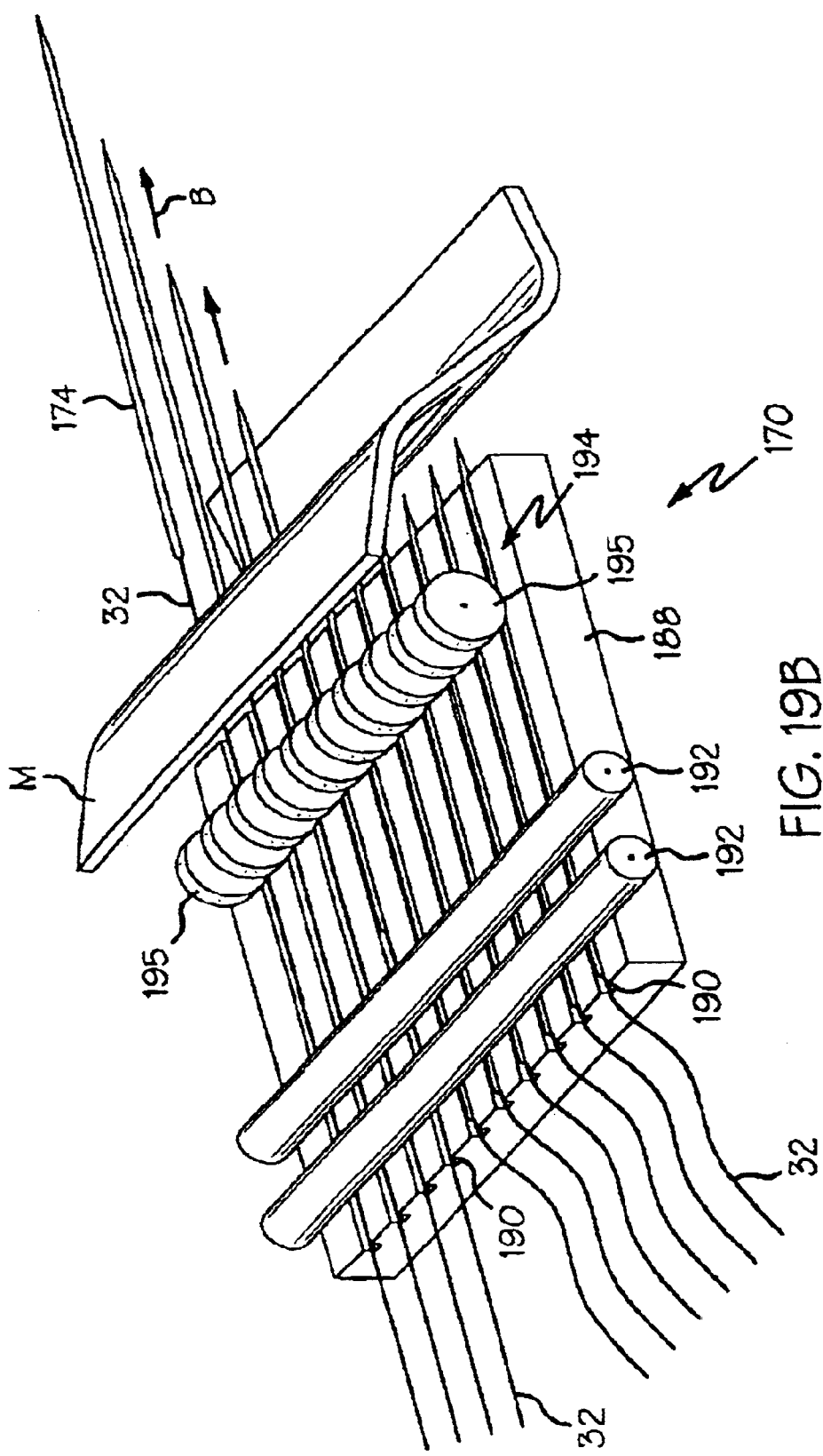
FIG. 19B is a perspective view of an alternative embodiment of an inserter made in accordance with the present invention.

Alternatively, the inserter 170 may include a plurality of rollers 195, as exemplified in FIG. 19B, whereby the needles 174 can be advanced or propelled individually or in a group, in a sequence, as opposed to all the needles 174 in the inserter 170.

Inserter 170 also may include one or more retaining bars 192 to assist in maintaining the needles 174 in the slots 190 as the are being advanced. As illustrated in FIGS. 19A and 19B, retaining bars 192 may take the form of rollers, or strip guides (not shown).

Rollers 195 can be rotated in a rotational direction R by used of a spring driven, pneumatic, hydraulic or electric motor with appropriate gearing that is connected to the rollers 19S.

To assist in advancing or propelling the needles 174 out of the inserter 170 and into the muscle M, needles 174 may have various structural configurations to so that a needle advancer can mechanically advance the needles 174, or to assist in manually advancing the needles 174. Needles 174 used with the present invention should be configured whereby the needle 174 can be inserted through muscle, such skeletal muscle. Needle 174 can be either a straight or curved needle that can be used in surgical procedures. Needles 174 used with the present invention should be sufficiently long and strong so that they can be inserted, either advanced or propelled through muscle. In a preferred embodiment, the needles 174 may include a straight needle having a tapered-point configuration with a length of about 6 cm.

Turning now to FIGS. 20A to 20D, the needle 174 may include a fin 174C that is affixed or attached to the proximal portion 174B of the needle. Fin 174C should be configured so that it protrudes out of the slot 190 (see, e.g., FIG. 19B) and so that the needle 174 can still slide along slot 190. The fin 174C is preferably detachable from the body of the needle 174 so that is may be snapped off as the needle 174 is advanced through the muscle M. The fin 174C also preferably can be made of a bioabsorbable material to minimize the need for collection and removal of the fin 174C from the body when they are snapped off. Illustrative examples of materials suitable for use as fin 174C in the present invention may include polymers, ceramic, and the like.

Figure 20A:
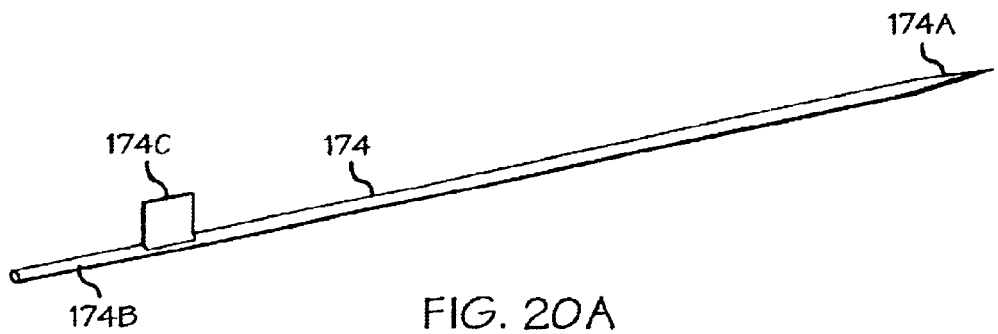
FIG. 20A is a perspective view of an alternative embodiment of a needle made in accordance with the present invention.
Figure 20B:
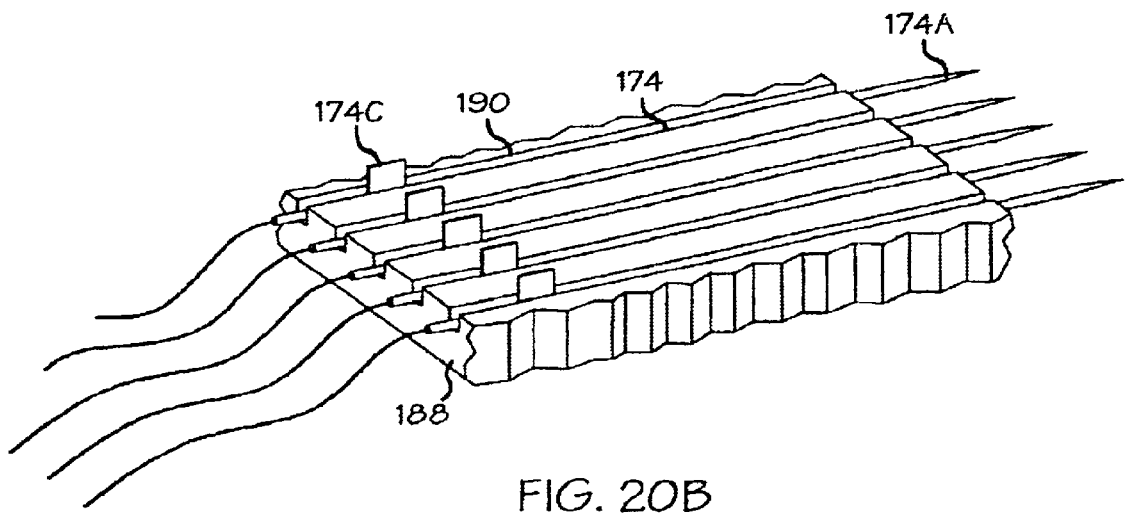
FIG. 20B is a partial perspective view of an inserter made in accordance with the present invention with the needle of FIG. 20A.
Figure 20C:
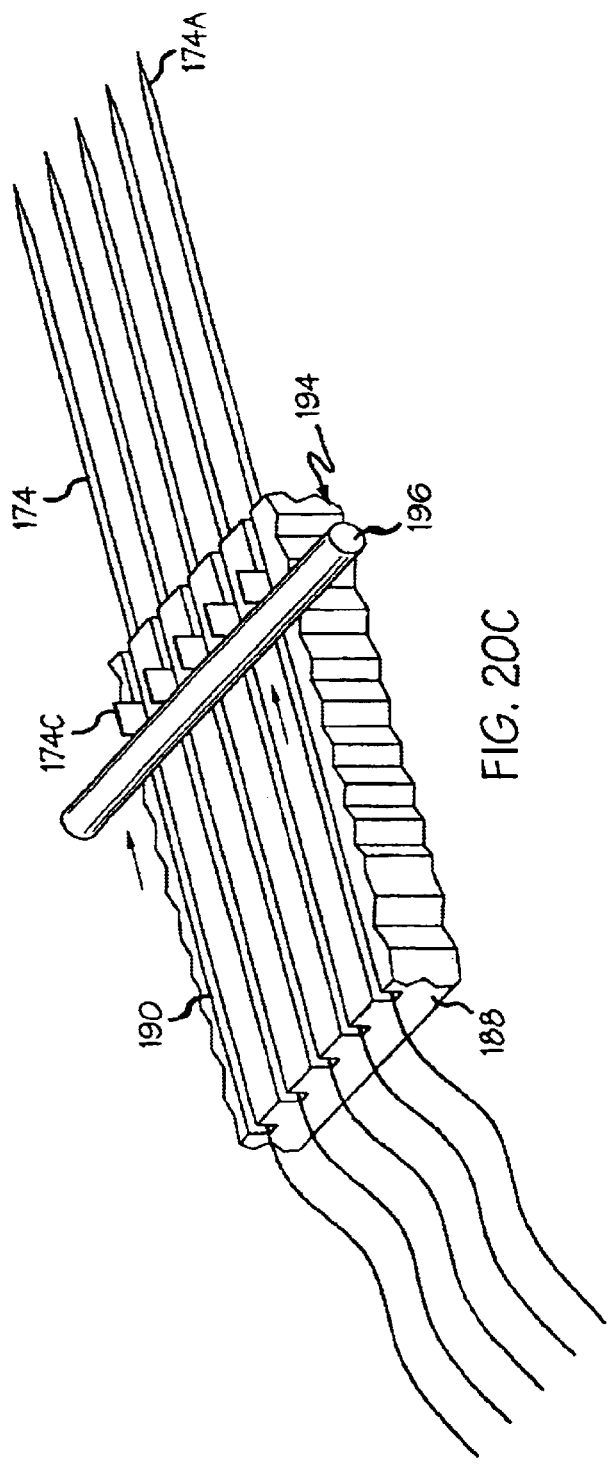
FIG. 20C is a perspective view of the inserter of FIG. 20B with a needle advancer.
Figure 20D:
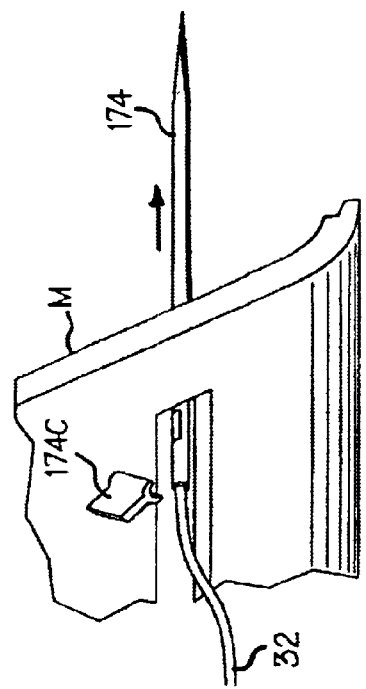
FIG. 20D is a perspective view of the needle of FIG. 20A with a detachable fin.

When using a needle 174 with a fin 174C, the needle advancer 194 can take the form of a bar 196, as exemplified in FIG. 20C, that assists in mechanically driving the needles 174 along the slots 190 and into the muscle M as illustrated by directional arrow A.

Needle 174 may include an indentation or perforation 174D, as exemplified in FIGS. 21A and 21B, and preferably in the distal portion 174B of the needle 174 that can be used to assist in advancing or propelling the needle 174 along the slot 190 and into the muscle M. A thimble 197, either manual (e.g., hand held) or mechanical mechanism, may be used with a needle 174 having an indentation 174D.

Figure 22:
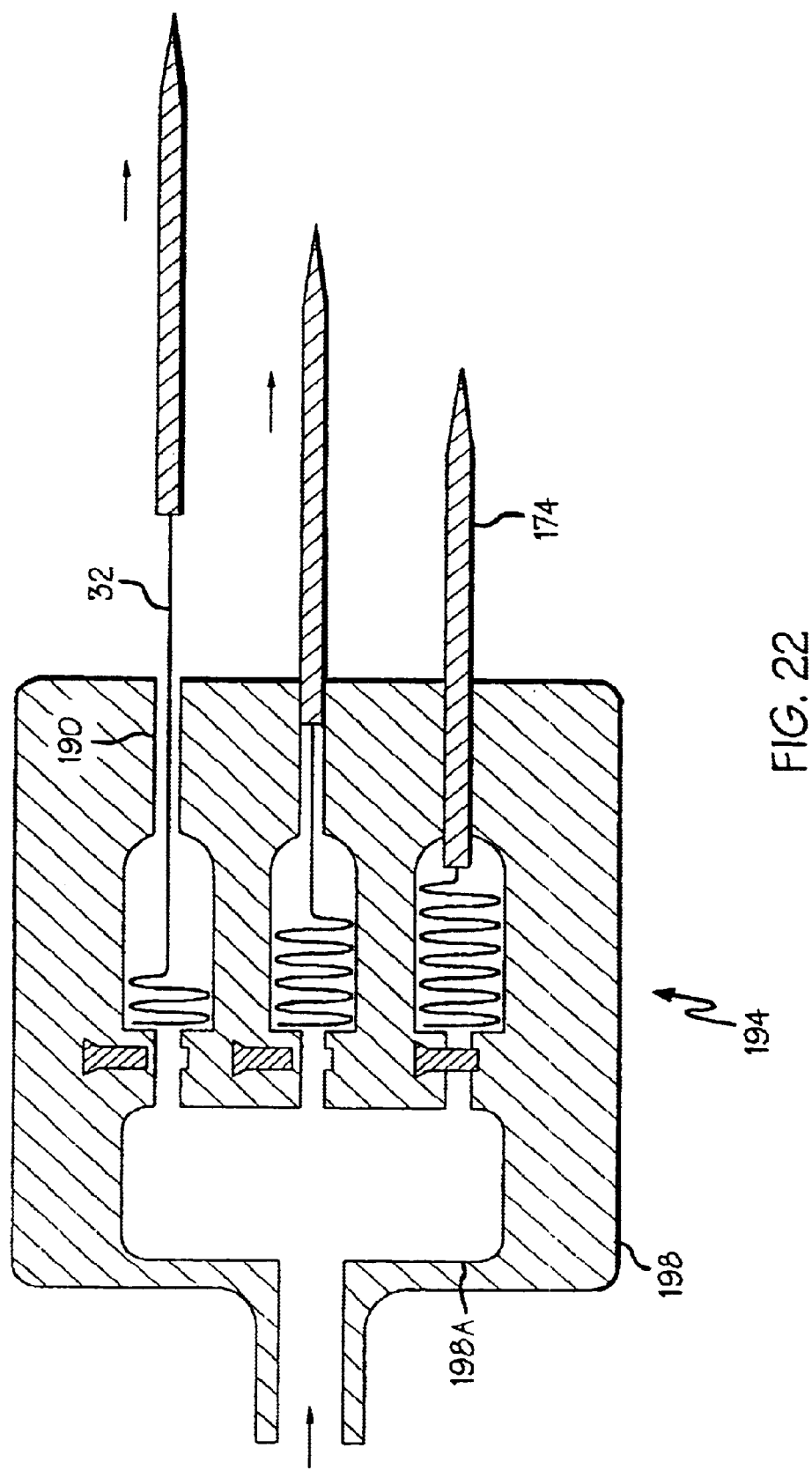
FIG. 22 is a partial cross-sectional view of an alternative embodiment of an inserter made in accordance with the present invention.

Besides manual and mechanism mechanisms to advance needles, the present invention also contemplates that other assemblies, mechanisms, or systems may be used to assist in advancing or propelling needles 174 into muscle M. As exemplified in FIG. 22, a pneumatic device 198 can be configured and used to advance needles 174. The pneumatic device 198 can include one or more slots or tubes 190 which are configured and adapted to receive needles 174. An application of pressurized fluid (e.g., gas or liquid) can advance or propel the needle 174 out of the pneumatic device 198. Chamber 198A within the pneumatic device 198 can be configured and adapted such that the needles 174 can be advanced all at once, or sequentially in a predetermined and/or selective sequence.

Alternatively, needle advancer 194 can take the form of a spring-loaded needle advancer 199, as exemplified in FIG. 23, which includes slots 190 configured and adapted to receive a needle 174 and permit the needle 174 be advanced or propelled therethrough. A retainer or lock 199A may be used to hold a needle 174 within the slot 190 under spring pressure until it is to be advanced or propelled into the muscle M. In a preferred embodiment, a needle 174 with one or more indentations 174D (see FIGS. 21A and 21B) may be used with restrictor 199A to frictionally and/or manually restrict movement of the needle 174 and to assist in maintaining the needle 174 in slot 190 under pressure. Once the releaser 199A is released from engaging the needle 174, the needle 174 can be advanced or propelled into the muscle M.

Open heart thoracic surgery may be required to implant the circulatory assist device PD. Alternatively, components of the circulatory assist device (e.g., PD) may be placed and positioned by insertion of components into the chambers of a beating heart and/or peripheral blood vessels. Clinically sufficient anesthesia is administered and standard cardiac monitoring is employed to the patient and then, if needed, the thoracic cavity, where the heart is usually situated, is opened using standard thoracic surgical procedures, which are known to those skilled in the art.

Once the thoracic cavity is opened, if an open heart procedure is to be employed in the present invention, circulation of blood to the natural heart (e.g., inflow and outflow) should be bypassed so the present invention can be inserted on and/or into the patient. Either the superior vena cava and the inferior vena cava, or the right atrium, and the aorta or other artery are preferably cannulated. The circulatory system is connected to as a cardiopulmonary bypass machine so that circulation and oxidation of the blood are maintained during the surgical procedure.

When using an artificial heart, the natural heart is removed and replaced by an artificial heart, such as the one disclosed in U.S. Pat. No. 4,904,225 (Chareire, et al), the disclosure of which is hereby incorporated herein by reference. When retaining the natural heart and using an assist device, the assist device, such as an intraventricular pump, a ventricular assist device or a heart harness, are positioned in and/or around the natural heart, as desired.

The muscle(s) M preferably for use with the present invention should be nonessential to other vital or important body functions. Moreover, the muscle(s) M should be capable of developing enough power or force to power a circulatory assist device without showing fatigue that could decrease energy output. Illustrative examples of muscle(s) M which may be suitable in the present invention include skeletal muscle, such as a dorsal muscle, and more preferably, the latisimus dorsi muscle, a limb girdle muscle, such as one or both of the psoas major muscles, a ventral muscle, such as the rectus abdominous muscle, or a muscle from a lower limb, such as the gracilis or the vastus lateralis muscles.

The detached end of the muscle(s) M is prepared for attachment to the prosthetic coupling 10, preferably by still allowing the muscle M to operate in its normal line of action with disturbing its blood supply. The tendon(s) T or an end of the muscle M selected for use with the present invention, generally the terminal or distal end, can be dissected and disconnected at or adjacent its musclotendonious junction or other junction (e.g., musculoaponeurotic junction) using standard surgical techniques.

The skeletal muscle M for use with the present invention is also preferably conditioned, such as with a low frequency stimulation, so that the muscle M becomes conditioned from a fast twitch muscle to a fatigue resistant muscle. In certain applications, the muscle may be paced during a conditioning period of about a month. During this conditioning period, the muscle M is subjected to a stimulation of about 2.5V, a frequency of about 50 Hz, and a pulse width of about 100 $\mu$sec. Furthermore, the pulses may progress over the conditioning period from about one pulse to about four pulses per train, stimulating about 30 times per minute throughout the conditioning period.

The filaments 14 of the second portion 30 are configured so that they can be gathered into a plurality of easily separable tows or bundles 32, and then swagged into an instrument for sewing an/or embedding the filaments 14 into the muscle, such as a tapered needle 174 (either straight or curved), or other surgical instrument.

Figure 10:
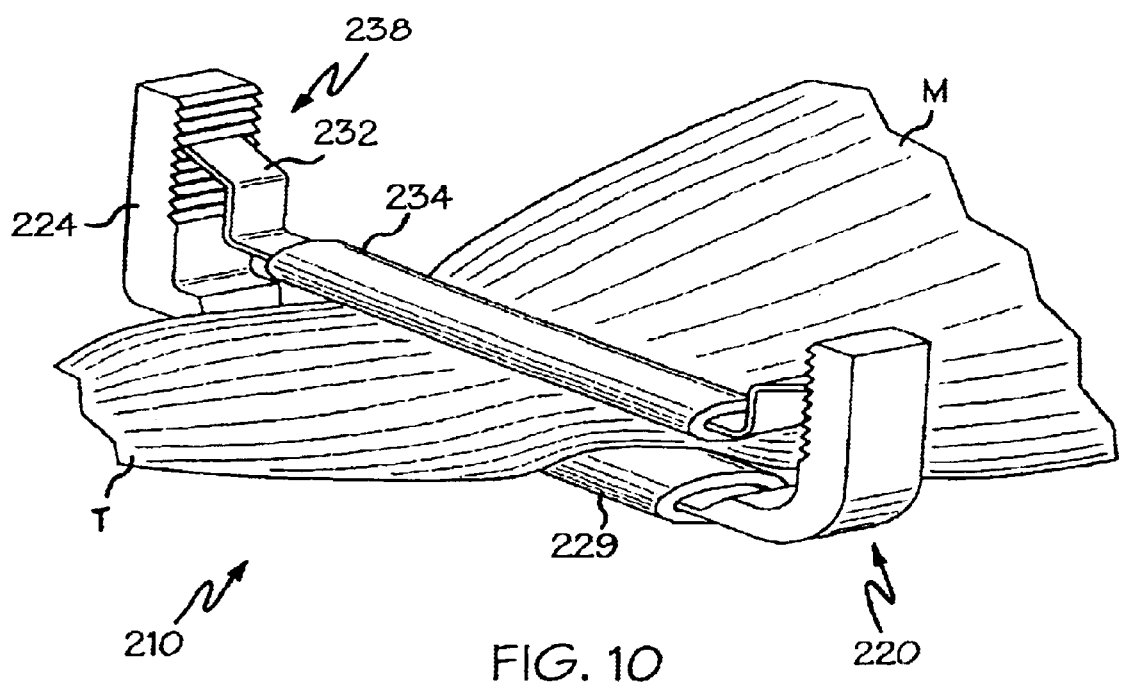
FIG. 10 is a perspective view of yet another holder made in accordance with the present invention.

The terminal or distal end of the muscle M is preferably extended and attached to a holder 110, such as by suturing it to a strip 140 by using one or more sutures 142 (see, e.g., FIGS. 5–7), impaling it on a rake 114 (e.g., FIGS. 8A to 8B), and/or mechanically holding it with a clamp 120 (see, e.g., FIGS. 9A to 10). The muscle M is held in place to facilitate delivery of tensile stress to the fibers in the muscle M, and to control the orientation of those fibers in the muscle M for desired insertion of the filaments 14 therein.

Preferably, once the muscle M is attached to a holder 110, a guide 150 can be used to assist in establishing a predetermined shape and location for a surface (e.g., S1 or S2) of the muscle M, illustrative examples of guides 150 usable with the present invention include rollers 152 (see, e.g., FIGS. 11A to 11B) whereby the muscle M is positioned and tensed around the rollers 152 (see, e.g., FIG. 11A) or around the rollers (see, e.g., FIG. 11B) in a taut condition. Another example of a suitable guide 150 used with the present invention is a plate 154 with displacing mechanism 156 (see, e.g., FIGS. 12 to 14) whereby the muscle M is compressively held therebetween. Furthermore, a guide 150 of the present invention may also include a plate 154 with a zone of underpressure 155 (see, e.g., FIGS. 15A and 15B) whereby a surface of the muscle M is placed on the plate 154 and an underpressure or vacuum through pores 64 hold the muscle in a tensed condition on plate 154.

Alternatively, or in conjunction with clamp 1, the needles 174 can be advanced or propelled into the muscle M using an inserter 170 for assisting in advancing all the needles 174 at once, or sequentially in a predetermined pattern. Inserter 170 can take the form of devices to advance the needles along a frame 106, such as a clasp 172 (see, e.g., FIGS. 17A to 17C), and a bar of embedded needles 182 (see, e.g., FIGS. 18A and 18B).

When using a clasp 172 with the present invention, the needles 174, with tows 32 attached thereto, are positioned in the slots 177 with the tip 174A of the needles 174 1;4 preferably facing or pointing toward the muscle M. The needles 174 are preferably held in place in the slots 177 in the desired orientation and position by use of a bar 178 that can be selectively moved to close the clasp 172 (See, e.g., FIG. 17C). Then, the inserter 170 can be advanced manually using surgical instrument I or along the frame 106 whereby the needles 174 are moved through the muscle M and the tows 32 and inserted into the muscle M.

When using the bar of embedded needles 182, the bar is can be advanced manually using clamp or surgical instrument I or along the frame 106 whereby the needles 174 are moved through the muscle M and the tows 32 and inserted into the muscle M. Thereafter, the bar 182 can be broken into at least two (2) pieces 184 and 186 so that the needles 174 and tows 32 can be advanced further into the muscle M and so that the bar 182 can be removed.

Also, inserter 170 can take the form of a device to advance the needles 174, either all at one or sequentially (see, e.g., FIG. 19B), relative to the inserter 170. Examples of such a device include a needle advancer 194 (see, e.g., FIGS. 19A to 21B), a pneumatic advancer 198 (see, e.g., FIG. 22), or an spring loaded advancer 199 (see, e.g., FIG. 23).

When using a needle advancer 194, the needles 174, with tows 32 attached thereto, are positioned and oriented in slots 190 of the inserter 170 so that the tip 174A of the needles 174 are preferably facing the muscle M. Thereafter, a needle advancer 194 is activated whereby the needles 174 and tows 32 advance toward, into and through the muscle M along the slots 190, as exemplified by arrow B in FIG. 19B.

Each bundle 32 is then sewn or woven into the end portion of muscle M in a distribution pattern so that the tension on the filaments 14 will affect lateral compressive 10: forces on the muscle M during its contraction that will sum with the interstitial pressure during muscle contraction.

The distribution pattern of filaments 14 should also be such that muscle tissue is interposed between the filaments 14 and such that the sum of the shear forces of the filaments 14 would sustain tensile forces while maintaining hydrostatic pressure and normal forces at or below normal physiological values. A sinusoidal pattern or an oblique S shaped pattern can assist in satisfying these conditions and also can assist to enhance filament 14 integration in the muscle M and insinuation of muscle tissue between the filaments 14.

Figure 24A:
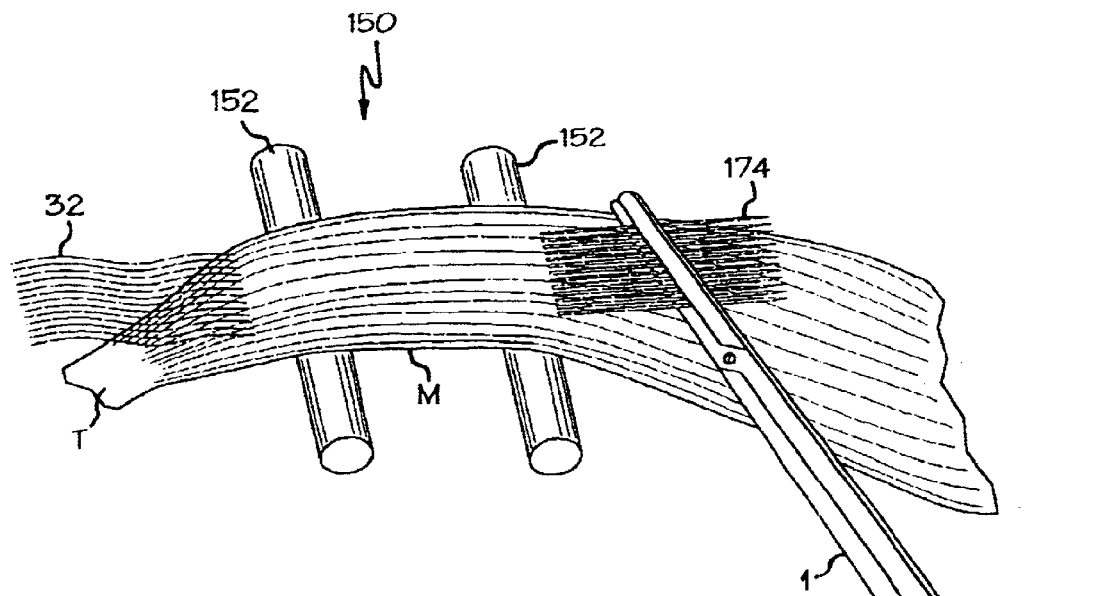
FIG. 24A is a perspective view of the needles and tows being grasped for pulling through after being inserted into the muscle in accordance with the present invention.
Figure 24B:
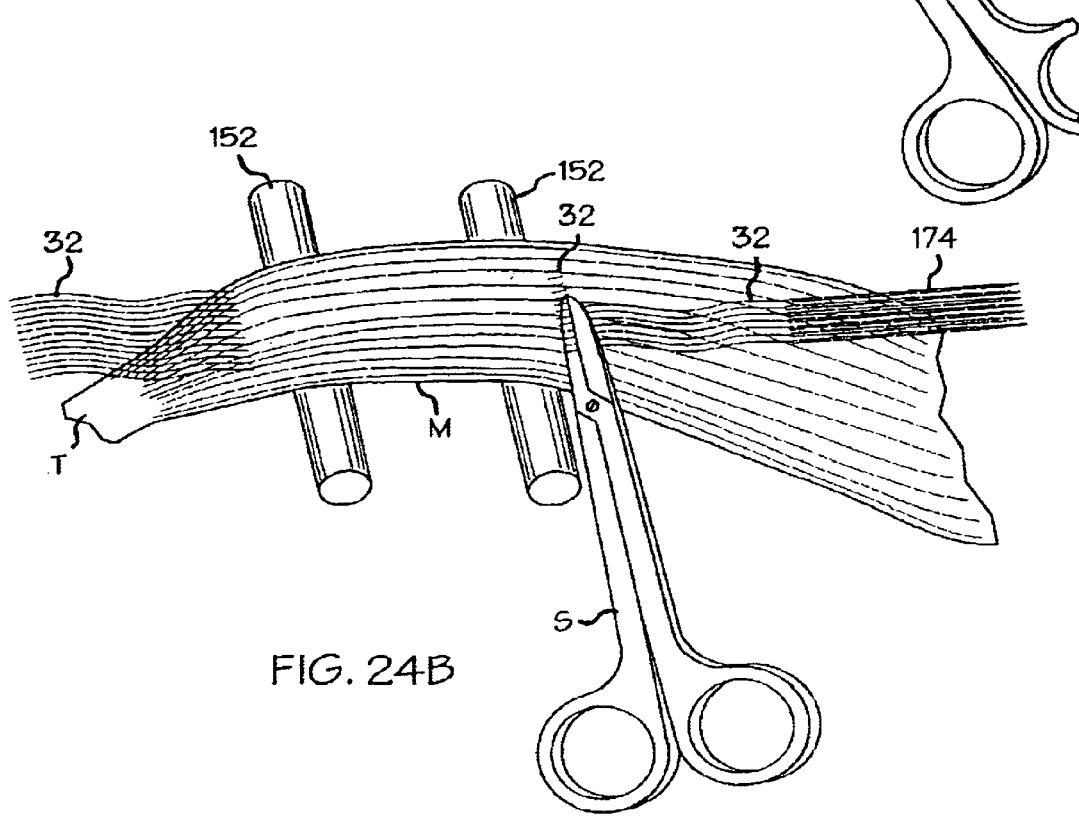
FIG. 24B is a perspective view of the tow of FIG. 24A being cut in accordance with the present invention.

Once inserted into the muscle M, the needles 174 and tows 32 can be manually withdrawn from the muscle M, as exemplified in FIG. 24A using a clamp I. Needles 174 can be passed through a superficial surface (e.g., S1) of the muscle. Once the needles 174 are withdrawn, they are separated from the tows 32 and filaments 14. Scissors S can be used to cut tows 32, as exemplified in FIG. 24B near the surface S1 of muscle M. Alternatively, a portion of the filaments 32 can be left dangling out of the muscle M. If the bundles and filaments 14 are left dangling out of the muscle M, then they may be tied off with a knot or suture using technique known in the industry. The other end of the coupling 10 can be attached and/or secured to a prosthetic device PD using a mechanical linkage device, such as a clamp, so that the muscle M can actuate it using prosthetic coupling 10. Attachment of prosthetic coupling 10 to the prosthetic device PD can be accomplished using apparatus and techniques known in the industry.

The inverted frustoconically shaped portion 44 of the sleeve 40 can be unfolded, positioned or straightened out to generally envelope a portion of the terminal end of the muscle M. Covering the portions or areas of the muscle M with sleeve 40, and preferably the frustoconically shaped portion 44, wherever filaments 14 protrude can reduce the possibility of scar tissue formation. Moreover, portion 44 can be trimmed so that only the exposed filaments 14 remain covered thereby assisting to decrease the expected healing/integration time of the filaments 14. By trimming the sleeve 40, and preferably the frustoconically shaped portion 44, fluids and/or blood can drain away from the incisions of filaments 14 into the muscle M, and thus be absorbed by surrounding tissue. Also, by trimming the frustoconically shaped portion 44, the potential for kinking of the sleeve 40 during muscle contraction is reduced. The frustoconically shaped portion 44 can also be attached or tacked to the muscle M to prevent movement by sewing small sutures in the portion 44 and the muscle M.

A muscle stimulator 80, such as a pulse generator, is preferably implanted and attached to the body. An electrical lead 82 of the stimulator 80 is preferably attached at or adjacent the muscle motor nerve for assisting in stimulating the skeletal muscle M so that it contracts, as desired.

Cardiotomies, if any, are closed, and the prosthetic coupling 10 is attached to the circulatory assist device PD using a junction device 50.

Once the circulatory assist device PD is properly positioned and secured, termination of a cardiopulmonary bypass, if used, is attempted and, if successful, the thoracotomy is closed.

Alternatively, it is contemplated that the prosthetic coupling 10 of the present invention could also be used as an artificial tendon to connect muscle M to bone.

Having shown and described the preferred embodiments to the present invention, further adaptations of the activation device for the living heart as described herein can be accomplished by appropriate modifications by one of ordinary skill in the art without departing from the scope of the present invention. For example, the present invention can be used as an artificial tendon to connect muscle to bone. Several such potential modifications have been discussed and others will be apparent to those skilled in the art. Accordingly, the scope of the present invention should be considered in terms of the following claims and is understood not to be limited in the details, structure and operation shown and described in its specification and drawings.

I claim:

1. An insertion kit for positioning a plurality of filaments into muscle, comprising:
    at least one holder that is configured for being attached to an end portion of the muscle;
    a frame coupled to the holder for maintaining the muscle in a position;
    a guide configured for engaging the muscle and for conforming the muscle secured to the holder to a desired shape;
    an inserter operating in conjunction with the holder and guide and operable for actively inserting the plurality of filaments into the shaped muscle proximate the guide, the inserter having a plurality of slots, each configured to receive a needle.

2. The insertion kit of claim 1, and wherein the at least one holder has a first portion configured for attachment to the end portion of a muscle, and a second portion configured for attachment to the frame.

3. The insertion kit of claim 1, wherein the at least one holder comprises a prosthetic strip configured for attachment to the end portion of a muscle.

4. The insertion kit of claim 1, wherein the at least one holder comprises a row of teeth configured for grasping the muscle.

5. The insertion kit of claim 1, wherein the at least one holder comprises a clamp.

6. The insertion kit of claim 5, wherein the clamp comprises a first portion and second portion that are selectively movable between an open position and a closed position.

7. The insertion kit of claim 5, wherein the clamp comprises at least one serrated surface.

8. The insertion kit of claim 5, wherein the clamp comprises at least one soft surface.

9. The insertion kit of claim 5, wherein the clamp comprises taper point penetrating pins.

10. The insertion kit of claim 1, comprising a plurality of holders.

11. The insertion kit of claim 1, wherein the guide comprises a plurality of bars.

12. The insertion kit of claim 1, wherein the guide comprises a plate.

13. The insertion kit of claim 12, wherein the guide comprises a plurality of plates, and the plurality of plates are oriented relative to each other such that a portion of the muscle is interposed between the first and second plate.

14. The insertion kit of claim 13, comprising an attachment assembly for holding the plates against the muscle in compression.

15. The insertion kit of claim 12, wherein the guide comprises a cushion.

16. The insertion kit of claim 12, wherein the plate has a zone wherein a pressure differential is generated to support the muscle on the plate.

17. The insertion kit of claim 1, wherein the slots are longitudinally extending slots.

18. The insertion kit of claim 17, wherein the slots are generally parallel to each other.

19. The insertion kit of claim 1, wherein the frame includes a first and second oppositely disposed supports, and the inner surface of each support includes a longitudinally extending groove, the inserter being selectively slidable along the grooves.

20. The insertion kit of claim 23, wherein the inserter comprises a retainer to secure the needles in the slots.

21. The insertion kit of claim 1, wherein the inserter comprises a bar having a first portion and a second portion, and a crease between the first and second portion.

22. The insertion kit of claim 1, wherein the inserter comprises a plurality of slots.

23. The insertion kit of claim 22, wherein the inserter comprises a plurality of needles embedded in the bar.

24. The insertion kit of claim 23, wherein the inserter comprises a needle advancer operable to be able to advance needles along the slots.

25. The insertion kit of claim 24, wherein the needle advancer comprises a roller.

26. The insertion kit of claim 25, wherein the roller comprises a plurality of rollers, each roller being configured to advance a needle.

27. The insertion kit of claim 1, wherein the inserter comprises a pneumatic needle advancer.

28. The insertion kit of claim 1, wherein the inserter comprises a spring-loaded needle advancer.

29. The insertion kit of claim 1 further comprising a plurality of needles configured to be attached to the plurality of filaments.

30. The insertion kit of claim 29, wherein at least one needle comprises a fin.

31. The insertion kit of claim 29, wherein at least one needle comprises at least one indentation.

32. A method for coupling a prosthetic device having filaments to a muscle, comprising the steps of:
   (a) detaching the muscle from its attachment at one end;
   (b) attaching a holder to the end;
   (c) coupling the holder to a frame and positioning the muscle in a tense condition;
   (d) engaging the muscle with a guide and conforming the muscle to a desired shape;
   (e) with an inserter having a plurality of slots configured to receive needles, actively embedding the filaments in the muscle proximate the guide.

33. The method of claim 32, comprising the steps of:
   (f) providing a plurality of tows of the filaments, each tow connected to needle;
   (g) advancing the needles into the muscle with the inserter.

34. The method of claim 33, comprising the step of advancing the needles at once.

35. The method of claim 33, comprising the step of advancing the needles in sequence.

\* \* \* \* \*

UNITED STATES PATENT AND TRADEMARK OFFICE
CERTIFICATE OF CORRECTION

PATENT NO. : 6,733,510 B1
DATED : May 11, 2004
INVENTOR(S) : David B. Melvin

It is certified that error appears in the above-identified patent and that said Letters Patent is hereby corrected as shown below:

Title page,
Item [56], References Cited, U.S. PATENT DOCUMENTS, add

| -- 3,595,230 | 7/1971 | Suyeoka et al. | 206/365 |
| 5,846,255 | 12/1998 | Donn Casey | 606/120 |
| 5,849,019 | 12/1998 | InBae Yoon | 606/151 |
| 4,345,601 | 8/1982 | Mamoru Fukuda | 606/147 |
| 5,409,499 | 4/1995 | Sung S. Yi | 227/902 |
| 5,540,705 | 7/1996 | Meade et al. | 606/139 |
| 5,797,932 | 8/1998 | Min et al. | 606/151 |
| 6,159,224 | 12/2000 | InBae Yoon | 606/139 |
| 6,312,445 | 11/2001 | Fogarty et al. | 606/157 |
| 5,584,840 | 12/1996 | Ramzey et al. | 606/120 |
| 5,620,452 | 4/1997 | InBae Yoon | 606/151 |
| 5,366,459 | 11/1994 | InBae Yoon | 606/151 |
| 3,725,984 | 4/1973 | Adolf Wilhelm Graber | 28/107 |
| 6,165,186 | 12/2000 | Fogarty et al. | 606/157 |
| 6,299,621 | 10/2001 | Fogarty et al. | 606/151 |
| 5,766,250 | 6/1998 | Chervitz et al. | 606/72 |
| 5,417,683 | 5/1995 | I-Shen Shiao | 604/173 |
| 5,013,304 | 5/1991 | Russell et al. | 604/167.03 |
| 6,170,415 | 1/2001 | Inoue et al. | 112/163 |
| 5,411,481 | 5/1995 | Allen et al. | 606/139 -- |

Column 1,
Line 20, change "The natural heart. and" to -- The natural heart, and --
Line 62, change "susceptible to fatigue to a muscle with" to -- susceptible to fatigue, to a muscle with --

Column 2,
Line 63, change "of a muscles typical contractile force" to -- of a muscle's typical contractile force --

Column 4,
Line 45, change "an open position arid a closed position." to -- an open position and a closed position. --
Line 52, change "A Cushion may also be" to -- A cushion may also be --

Column 7,
Line 44, change "as will be detailed below and also" to -- as will be detailed below, and also --

UNITED STATES PATENT AND TRADEMARK OFFICE
CERTIFICATE OF CORRECTION

PATENT NO. : 6,733,510 B1
DATED : May 11, 2004
INVENTOR(S) : David B. Melvin

It is certified that error appears in the above-identified patent and that said Letters Patent is hereby corrected as shown below:

Column 8,
Line 22, change "kemmantel-type or" to -- kernmantel-type or --
Line 37, change "In one embodiments about 40 percent" to -- In one embodiment, about 40 percent --
Line 41, change "kemmantel-type cord" to -- kernmantel-type cord --

Column 9,
Line 66, change "TECOFLEX by Ternniocardio Systems of" to -- TECOFLEX by Thermocardio Systems of --

Column 10,
Lines 24-25, change "One or more holders may be utilized to hold a particular muscle or part of the muscle M." to -- The insertion kit may include a plurality of holders. --

Column 12,
Line 10, change "or screws assembly." to -- or screw assembly. --

Column 15,
Line 67, change "the muscle M, illustrative examples of" to -- the muscle. Illustrative examples of --

Column 16,
Line 14, change "with clamp 1, the needles 174 can be" to -- with clamp I, the needles 174 can be --
Line 24, change "of the needles 174 1;4 perferably facing or" to -- of the needles 174 perferably facing or --

UNITED STATES PATENT AND TRADEMARK OFFICE
CERTIFICATE OF CORRECTION

PATENT NO.    : 6,733,510 B1
DATED         : May 11, 2004
INVENTOR(S)   : David B. Melvin It is certified that error appears in the above-identified patent and that said Letters Patent is hereby corrected as shown below:

Column 16 (cont'd),
Line 56, change "lateral compressive 10: forces on the" to -- lateral compressive forces on the --

Signed and Sealed this

Nineteenth Day of October, 2004

JON W. DUDAS
*Director of the United States Patent and Trademark Office*